(12) United States Patent
Rosheim

(10) Patent No.: US 6,418,811 B1
(45) Date of Patent: Jul. 16, 2002

(54) ROBOTIC MANIPULATOR

(75) Inventor: Mark E. Rosheim, Minneapolis, MN (US)

(73) Assignee: Ross-Hime Designs, Inc., St. Paul, MN (US)

(*) Notice: Subject to any disclaimer, the term of this patent is extended or adjusted under 35 U.S.C. 154(b) by 0 days.

(21) Appl. No.: 09/579,903

(22) Filed: May 26, 2000

(51) Int. Cl.⁷ .............................................. G05G 11/00
(52) U.S. Cl. ....................... 74/490.06; 901/29; 414/729
(58) Field of Search ........................ 74/490.01, 490.05, 74/490.06; 901/27, 28, 29, 15; 414/729, 735

(56) References Cited

U.S. PATENT DOCUMENTS

| 125,880 | A | 4/1872 | Clemens |
| 2,988,904 | A | 6/1961 | Mazziotti ........................ 64/21 |
| 3,075,368 | A | 1/1963 | Hulse ............................. 64/20 |

(List continued on next page.)

OTHER PUBLICATIONS

"On the Development of the Agile Eye" by C. Gosselin et al., Dec. 1996.
P. 166 of *Machine Design*, Jun. 21, 1973.
P. 291 of *Mechanisms & Mechanical Devices Sourcebook*, by N. Chironis, entitled "Intertwining Links Produce True Constant–Motion Universal", 1991.
Pp 124 through 127 and 162 and 163 from *Robot Wrist Actuators* by Mark E. Rosheim, 1989.
Cover page and pp 90 and 92 from Dec. 1994 issue of *Discover* magazine.
Pp 131 through 133 from *Robot Evolution—The Development of Anthrobotics* by Mark E. Rosheim, 1994.
"Constant–Velocity Shaft Couplings" by K. H. Hunt, *Journal of Engineering for Industry*, May 1973.

*IEEE* publication "A Pantograph Linkage Parallel Platform Master Hand Controller for Force–Reflection", May 1992 by Gregory Long and Curtis Collins.
*IEEE* publication "HEXA: a fast six–DOF fully–parallel robot", by Pierrot, Dauchez and Fournier, 1991 (Figure 4).
Publication "A Coarse–Fine Approach to Force–Reflecting Hand Controller Design", by Stocco and Salcudean, dated Apr. 22, 1996 (Figures 6, 7 and 8).
*IEEE* publication "Kinematic Analysis of a Novel 6–DOF Parallel Manipulator", by Cleary, and Brooks, (Figure 2), 1993.
*IEEE* publication "A New Analytical System Applying 6 DOF Parallel Line Manipulator for Evaluating Motion Sensation", Mimura & Funahashi, 1995.

*Primary Examiner*—David Fenstermacher
(74) *Attorney, Agent, or Firm*—Kinney & Lange, P.A.

(57) ABSTRACT

A controlled relative motion system comprising a base support, a manipulable support, a group of link end constrainers each having a first portion movably connected to a second portion thereof so that ends of the first and second portions can be selectively separated from one another in a selected direction so as to have a selected distance therebetween, and two groups of pivoting links. With at least four link end constrainers in the group thereof, the first group of pivoting links has corresponding links each rotatably coupled to force imparting means or to the base support so as to be rotatable about a corresponding base link axis where each of said base link axes extend into regions between adjacent ones of said first group of pivoting links into which regions said base link axes of said adjacent ones also extend, and each coupled to a first portion end of a corresponding one of the group of link end constrainers. The second group of pivoting links each rotatably coupled to the manipulable support and a corresponding one of the group of link end constrainers second end. Four or more or less numbers of link end constrainers in the group thereof are useable in the form of straps or interconnected "eye" bolts with corresponding number of pivoting links in the two groups.

29 Claims, 16 Drawing Sheets

U.S. PATENT DOCUMENTS

| | | | |
|---|---|---|---|
| 3,477,249 A | 11/1969 | Culver | 64/21 |
| 4,396,344 A | 8/1983 | Sugimoto et al. | 414/735 |
| 4,651,589 A | 3/1987 | Lambert | 74/469 |
| 4,674,947 A | 6/1987 | Hamada et al. | 414/735 |
| 4,806,068 A | 2/1989 | Kohli et al. | 414/735 |
| 4,819,496 A | 4/1989 | Shelef | 74/479 |
| 4,976,582 A | 12/1990 | Clavel | 414/729 |
| 5,333,514 A | 8/1994 | Toyama et al. | 74/479 BW |
| 5,378,282 A | 1/1995 | Pollard | 118/697 |
| 5,420,489 A | 5/1995 | Hansen et al. | 318/568.18 |
| 5,556,242 A | 9/1996 | Sheldon et al. | 409/132 |
| 5,656,905 A | 8/1997 | Tsai | 315/568.21 |
| 5,699,695 A | 12/1997 | Canfield et al. | 74/940.06 |
| 5,715,729 A | 2/1998 | Toyama et al. | 74/490.03 |
| 5,771,747 A | 6/1998 | Sheldon | 74/248 |
| 5,865,063 A | 2/1999 | Sheldon | 74/490 |
| 5,893,296 A | 4/1999 | Rosheim | 74/490.03 |
| 5,979,264 A * | 11/1999 | Rosheim | 74/490.06 |
| 6,105,455 A * | 8/2000 | Rosheim | 74/490.06 |
| 6,196,081 B1 * | 3/2001 | Yau | 74/479.01 |

* cited by examiner

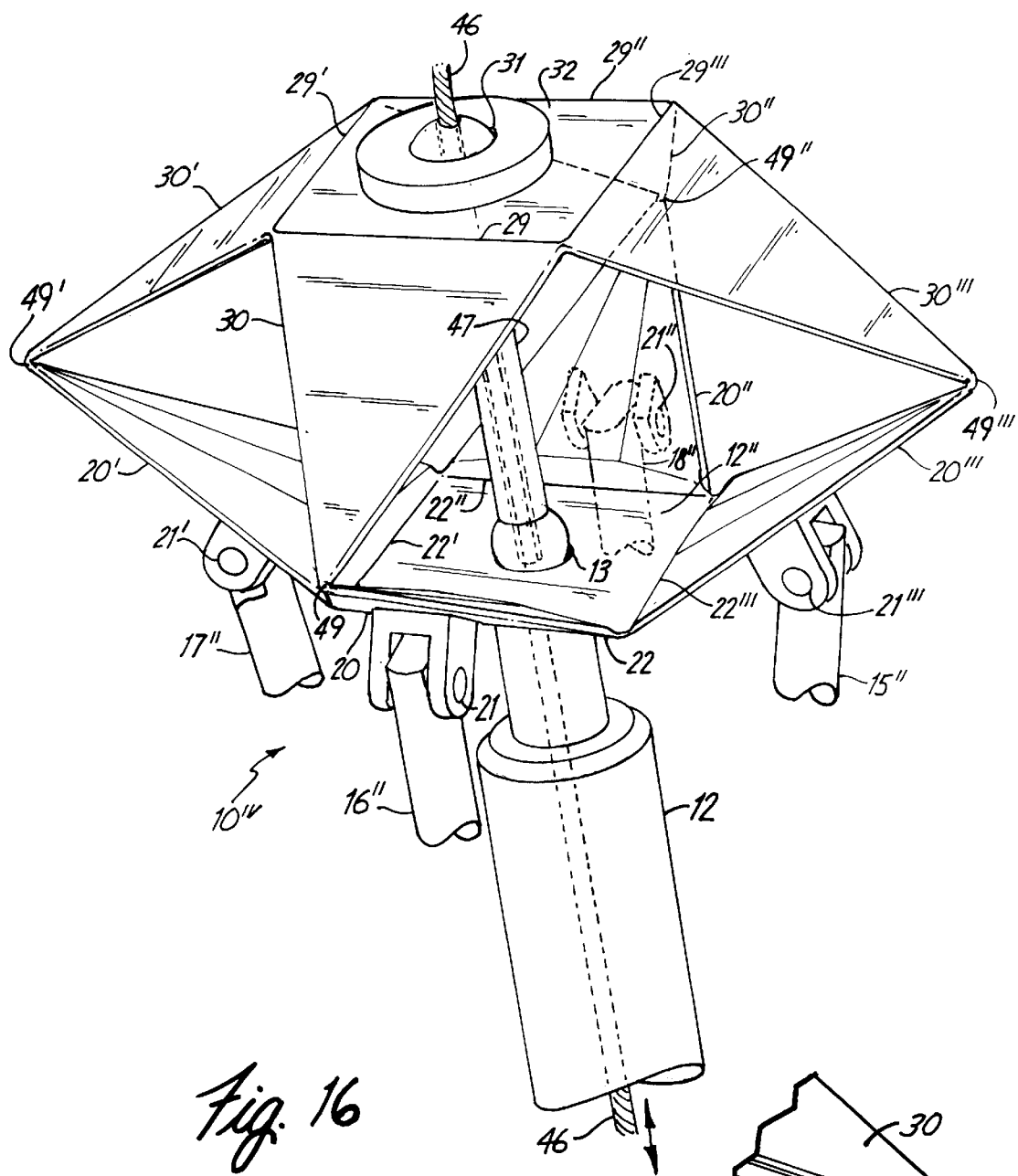
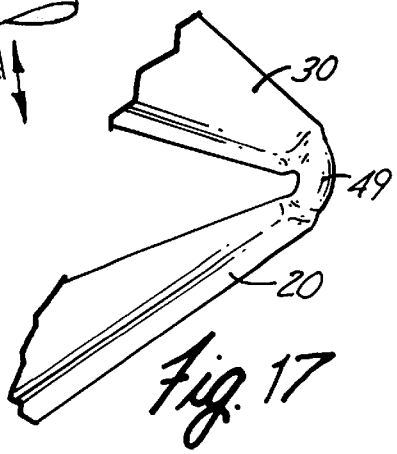
Fig. 16
Fig. 17

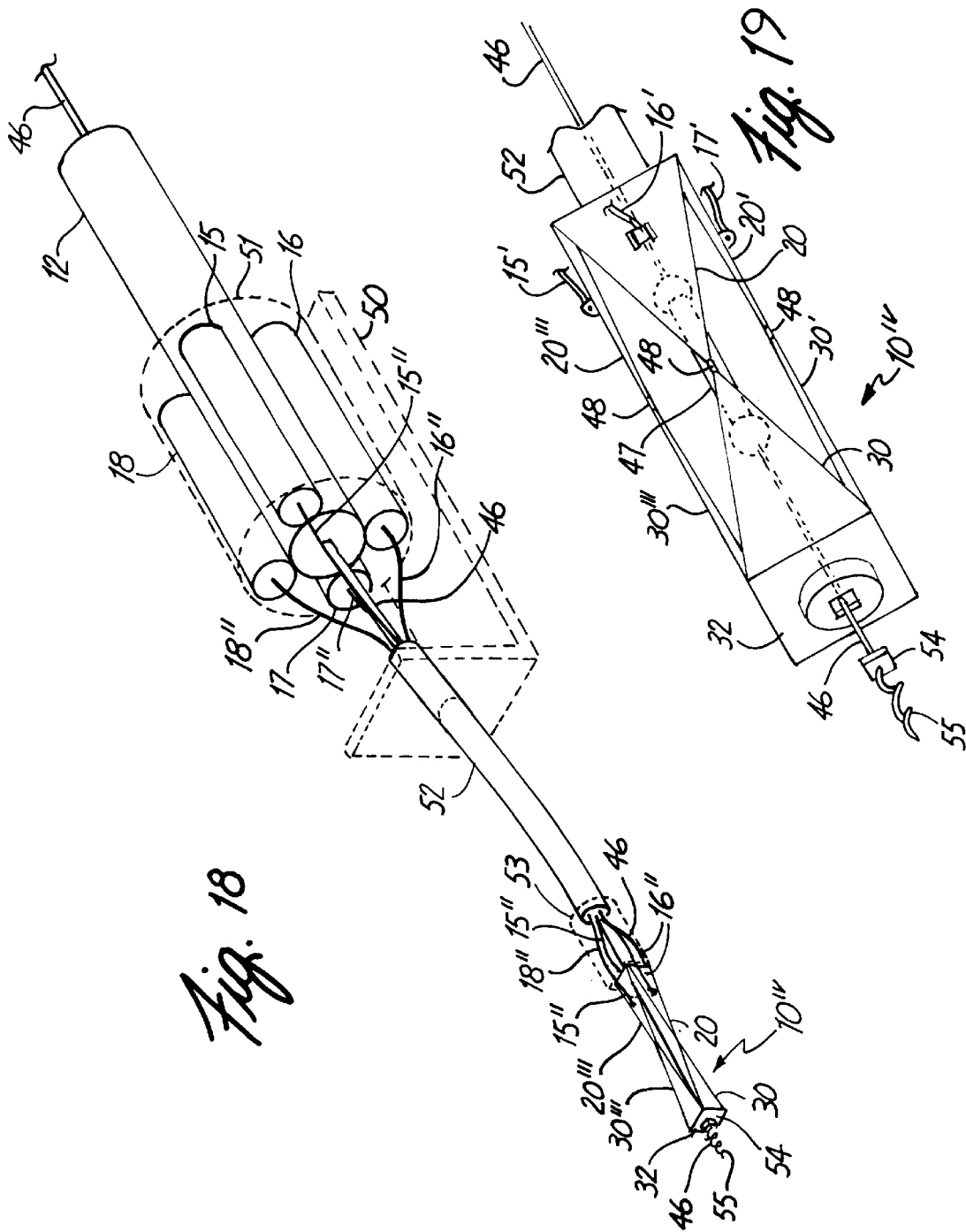

ROBOTIC MANIPULATOR

BACKGROUND OF THE INVENTION

A strong desire for increased automation in the workplace, and a desire to increase the use of animated figures depicting animals, humans or other characters in entertainment and other situations, along with an increased ability to control such mechanical manipulators has led to substantial efforts in the development of robotics. As a result, significant advances have occurred in many aspects of robotics.

Perhaps the most widely used controlled component in robotic systems is a mechanical manipulator, that portion of a robot used to change the position of orientation of selected objects engaged by that manipulator. In many instances, such mechanical manipulators are desired to have capabilities similar to those of the human wrist or shoulder, that is, exhibiting two (or in some instances, more) degrees of freedom of motion.

Although a number of such mechanical manipulators have been developed which to a greater or lesser degree achieve some of these desires therefor, most have been relatively complicated devices requiring complicated components and difficult assembly procedures or both. Many, in addition, represent compromises in having relatively limited range, or singularities within the ranges, or other limitations in performance. Thus, there is a strong desire for a mechanical manipulator which can, under control of the user, position objects anywhere over at least a hemispherical surface without any singularities in the operation of the device in this range, and which can be made both reliably and inexpensively.

One such mechanical manipulator meeting this desire comprises a base support, a pivot holder and a plurality of pivoting links. The pivoting links are rotatably coupled to both the base support so as to be arrayed by rotational axis radially thereabout and to members of the pivot holder to rotate about axes which extend in different directions for each of these rotatable couplings in a link typically in accord with specific geometrical arrangements, and in different directions from similar axes in another of such links. The pivot holder is linked with a second plurality of pivoting links to a manipulable support. Such systems can incorporate a variety of force imparting members to control movements of various ones of the pivoting links or pivot holder members with as few as two being required. Pivot holder members having hinged portions with one portion rotatably connected to a first plurality pivoting link and the other portion rotatably connected to a second plurality pivoting link provides a capability for controlling the separation between the base and manipulable supports, but requires an actuator for each first plurality pivoting link and has its manipulable support positioned less precisely.

Another manipulable support meeting this desire comprises a base support, a pivot holder with hinged members and three pivoting links. The pivoting links are rotatably coupled to both the base support, but this time to be arrayed by axis more or less tangentially thereabout, and to members of the pivot holder to rotate about axes which extend in different directions for each of these rotatable couplings in a link typically in accord with specific geometrical arrangements, and in different directions from similar axes in another of such links. The pivot holder is linked with another three pivoting links to a manipulable support. Such systems can incorporate a variety of force imparting members to control movements of various ones of the pivoting links or pivot holder members with three being required.

This latter mechanical manipulator has a stronger construction than the former in having the three pivoting links connected to the base support with the rotation axis for each positioned tangentially thereto rather than being more or less cantilevered radially therefrom. However, there is much less vertical support provided to loads on the manipulable support positioned at relatively extreme angles with respect to vertical in some radial positions. Furthermore, many of the piece parts must have surfaces that are other than perpendicular or parallel to one another requiring much expensive odd angle machining. In operation, the operation of any one actuator can not be controlled independently from the others because of the unavoidable coupling between the three pivoting links making control considerably more difficult. Thus, there is a desire for a mechanical manipulator that is economical, strongly constructed and capable of providing relatively good vertical support for output loads even at extreme angular positions.

BRIEF SUMMARY OF THE INVENTION

The present invention provides a controlled relative motion system comprising a base support, a manipulable support, a group of link end constrainers each having a first portion movably connected to a second portion thereof so that ends of the first and second portions can be selectively separated from one another in a selected direction so as to have a selected distance therebetween, and two groups of pivoting links. With at least four link end constrainers in the group thereof, the first group of pivoting links has at least four links therein each rotatably coupled to a force imparting means or to the base support so as to be rotatable about a corresponding base link axis where each of said base link axes extend into regions between adjacent ones of the first group of pivoting links into which regions said base link axes of said adjacent ones also extend, or both, and each coupled to a first portion end of a corresponding one of the group of link end constrainers. The second group of pivoting links has at least four links therein each rotatably coupled to the manipulable support so as to be rotatable about a corresponding support link axis and each coupled to the second portion end of a corresponding one of the group of link end constrainers. Various kinds of force imparting members can be used connected to the first group of pivoting links to position the manipulable support both in rotation and in translation as desired. These force imparting devices may be eliminated to provide a constant velocity rotatable, bendable joint, or they may be replaced by shock absorbers to provide an impact management device.

Four or more, or less, in number of link end constrainers in the group thereof are useable in the form of straps or interconnected "eye" bolts. A strand, often in the form of a cable, extending through the base and manipulable supports can be used to operate or position devices on or adjacent to the manipulable support through rotating or translating the strand, or through translating or rotating the manipulable support, or some combination thereof.

BRIEF DESCRIPTION OF THE DRAWINGS

FIGS. 16 and 17 show perspective and fragmentary views of another alternative embodiment of the present invention, and FIGS. 18 and 19 show a further embodiment of the invention shown in FIGS. 12 through 17.

DETAILED DESCRIPTION

Figure 1:
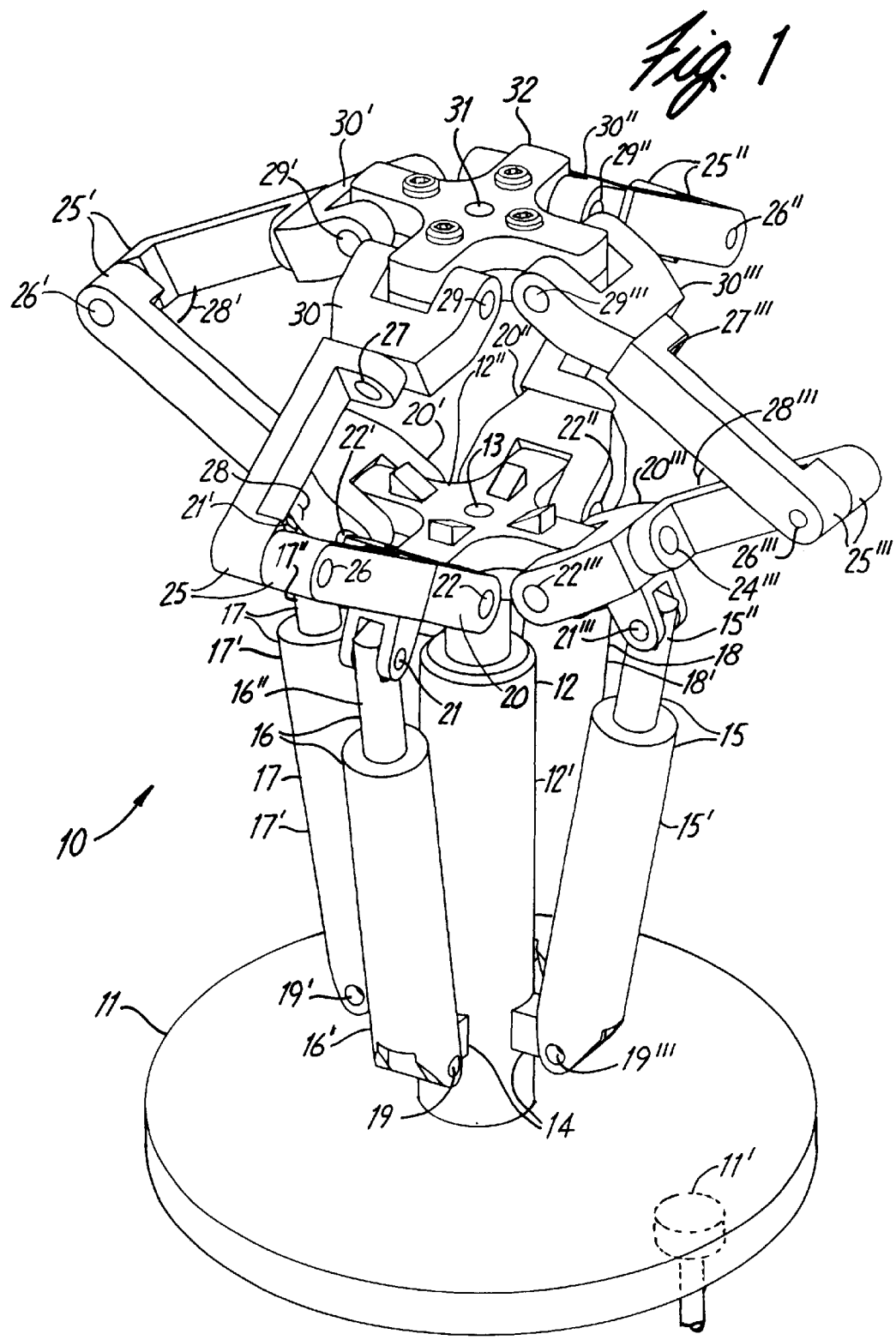
FIG. 1 shows a perspective view of an embodiment of the present invention.
Figure 2:
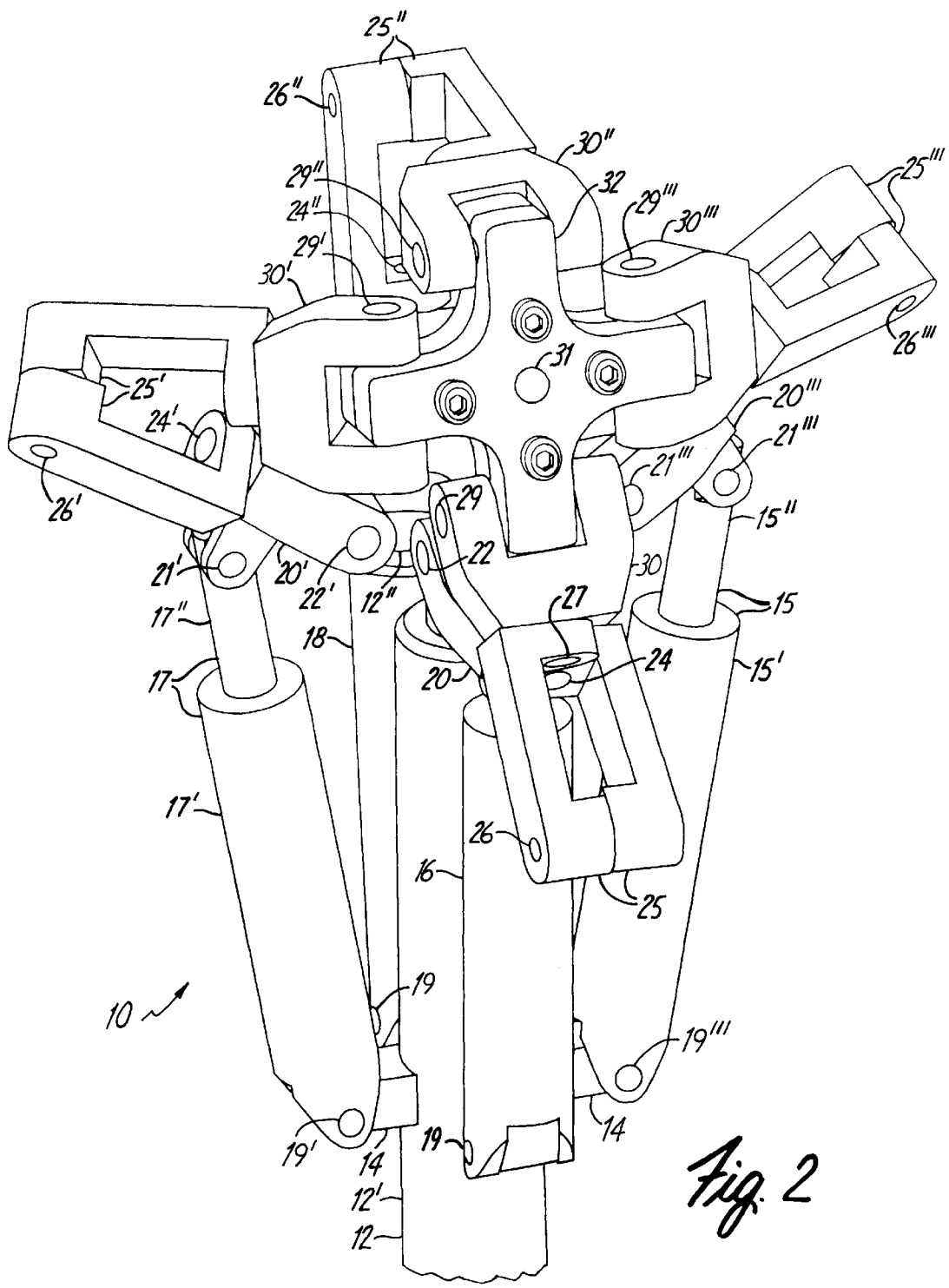
FIGS. 2 through 4 show various perspective views of the embodiment of the present invention shown in FIG. 1, FIGS. 5, 6, 7 and 8 show perspective views of alternative embodiments of the present invention shown in FIG. 1.
Figure 3:
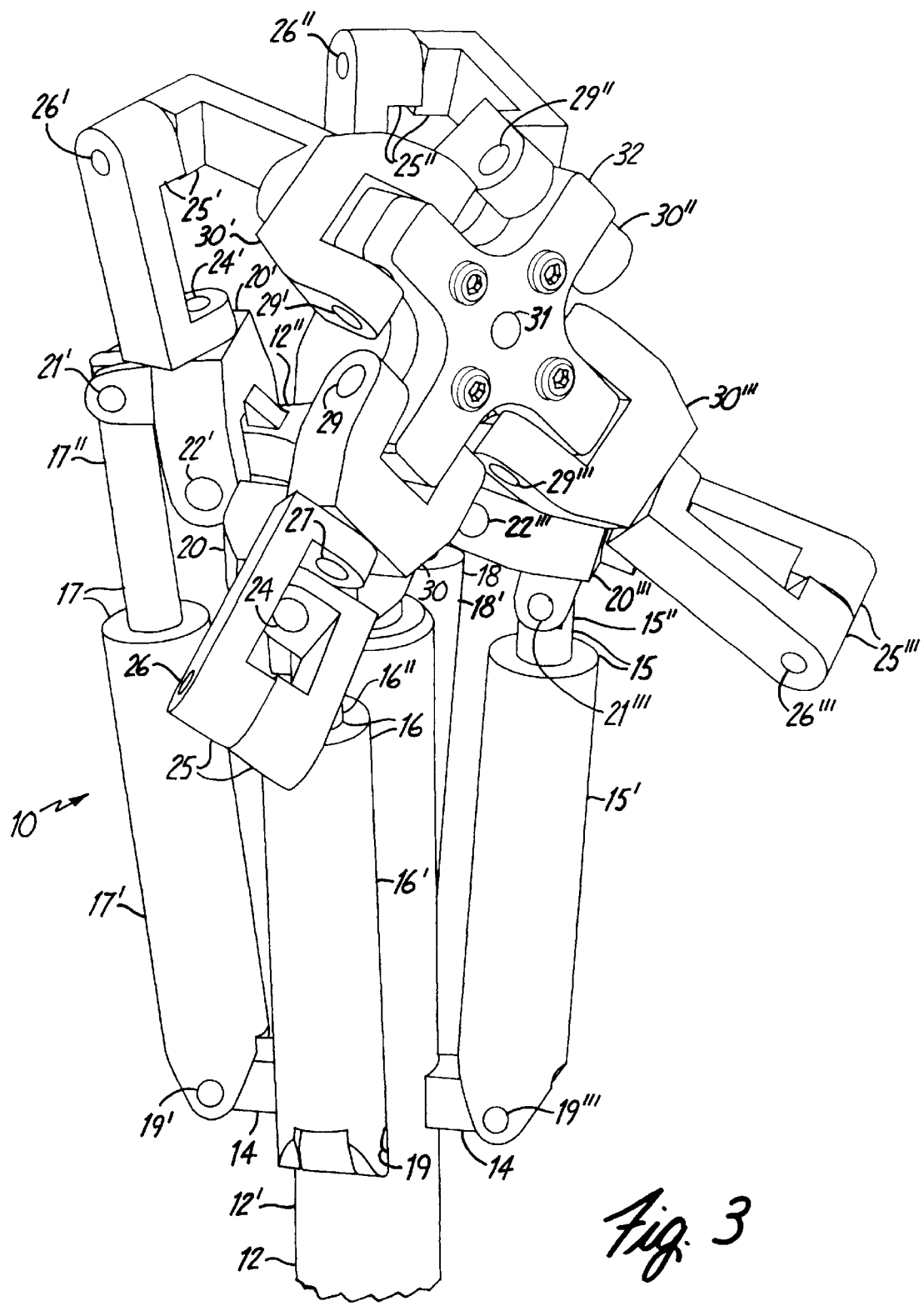
Figure 4:
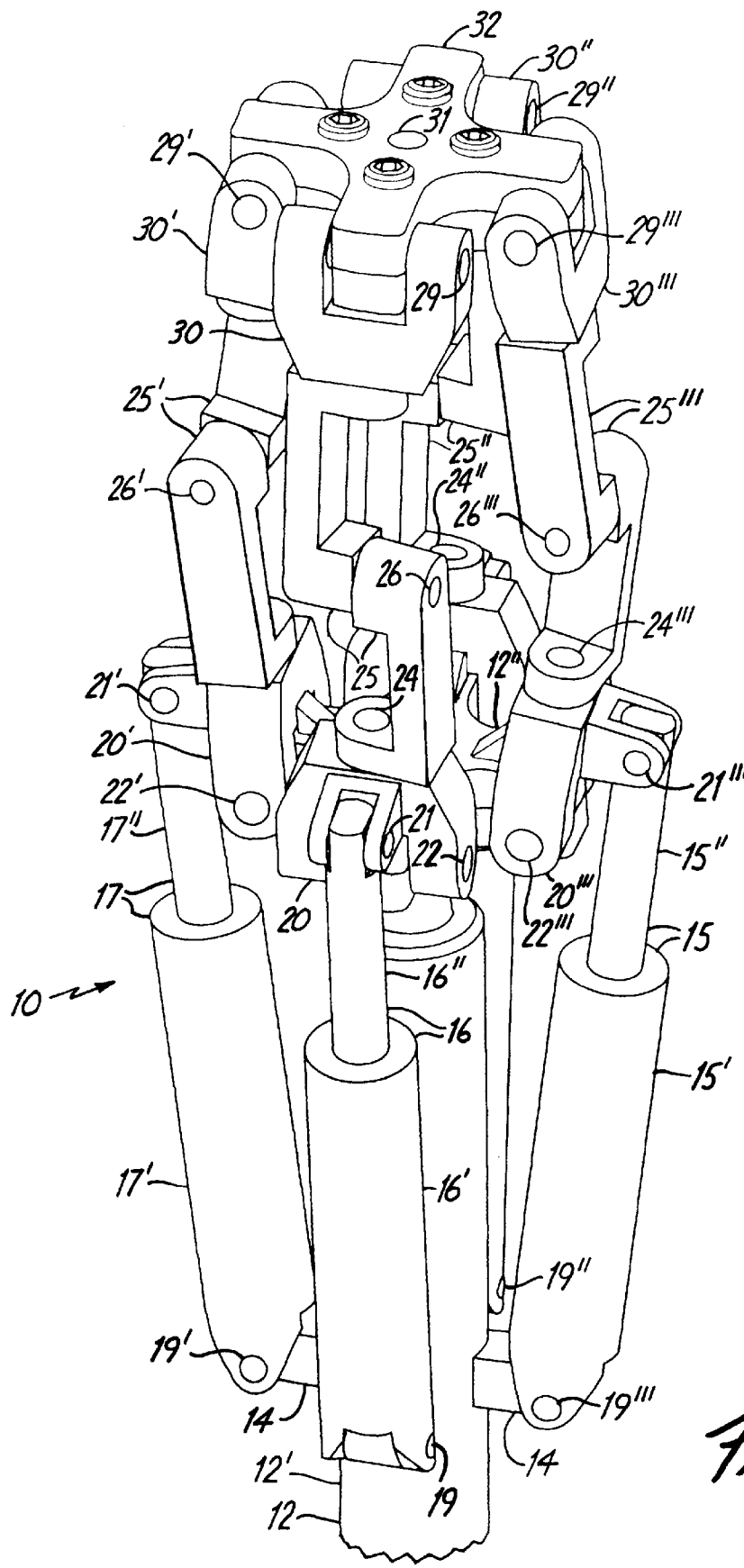

FIGS. 1, 2, 3 and 4 show a first embodiment of a mechanical manipulator, or controlled member motion system, 10, which can have a very large output operating range in various configurations over which it is free of singularities, and which is operated by various force imparting devices directly or through various drive trains. FIG. 1 shows a perspective view of manipulator 10 with FIGS. 2, 3 and 4 showing alternative positions of the output portion of manipulator 10. Manipulator 10 is positioned on a mounting arrangement, 11, containing therein an electric motor arrangement, unseen in these figures, which can rotate mounting arrangement 11 in either the clockwise or counterclockwise direction as selected by the user to thereby carry the remainder of joint or manipulator 10 correspondingly with it in these directions. Alternatively, an external electric motor arrangement, again not shown, can drive a shaft and pinion gear, 11', which meshes with an internal ring gear in mounting arrangement 11 to again provide for the rotation of mounting arrangement 11 in either the clockwise or counterclockwise direction as selected by the user.

Directly supported on mounting arrangement 11 is a base support, 12, shown as truncated cylindrical shell structure, 12', fixedly supporting a symmetrical cruciform shaped spider base, 12", though different geometrical shapes can be used. This symmetrical cruciform shape leads to spider base 12" having four spider arms extending outwardly from a central core with one pair of arms extending in opposite directions to one another, and the remaining pair also extending in directions opposite to one another which are also perpendicular to the directions of extent of the first pair. On top of each of these spider arms, at approximately the point where each begins extending outwardly from the central core, there is provided as part of the arm a wedge shaped stop to prevent further inward rotation of a corresponding pivoting link to be described below.

Support 12 has an opening, 13, extending vertically in these figures along the axis of radial symmetry for support 12 parallel to the outer curved sides of cylindrical shell 12' and perpendicular to the directions of extent of the arms of spider base 12". Opening 13 extends through support 12 and from there through mounting arrangement 11 along the axis about which it is capable of rotating manipulator 10 so as to be capable of permitting some desired means extend therethrough such as electrical wiring, optical fibers or some mechanical arrangement, or some combination thereof.

Also shown supported directly on cylindrical shell 12' are four linear actuator support bosses, 14, each of which is shown rotatably connected to and supporting a corresponding linear actuator. That is, four linear actuators, 15, 16, 17 and 18, are each rotatably mounted at the corresponding base thereof, 15', 16', 17' and 18', respectively, in the corresponding one of bosses 14 by a corresponding one of pivot pins, 19, 19', 19" and 19'" (with pin 19 connecting actuator 16 followed by pins 19', 19" and 19'" connecting actuators 17, 18 and 15, respectively) which extend perpendicularly to a radius of cylindrical shell 12'. Linear actuators have output shafts, 15", 16", 17" and 18", extending from the corresponding one of bases 15', 16', 17' and 18' an amount set by the clockwise or counterclockwise rotation of threaded output shafts of electric motors provided in those bases, not shown, with each such threaded shaft being engaged with a threaded inner surface wall of the corresponding base. Wiring interconnecting these linear actuator motors with a controller is not shown.

Output shafts 15", 16", 17" and 18" of linear actuators, 15, 16, 17 and 18 are each rotatably connected to a corresponding one of a plurality of pivoting links, 20, 20', 20" and 20'", by a corresponding one of a set of pins, 21, 21', 21" and 21'", respectively. Rotation by the rotor in the electric motors in linear actuators 15, 16, 17 and 18, clockwise or counterclockwise, causes the corresponding one of output shafts 15", 16", 17" and 18" to extend or retract to rotate that one of pivoting links 20, 20', 20" and 20'" to which it is rotatably connected. Such rotation occurs in one or the other of the rotational angular directions about that corresponding one of a set of pins, 22, 22', 22" and 22'", rotatably connecting these pivoting links to a corresponding one of the arms of spider base 12".

Pins 22, 22', 22" and 22'" are each positioned in and through its arm of spider base 12" such that the axis of rotation thereabout is oriented approximately perpendicular to a radius extending horizontally outward from the center of spider base 12" through that arm. In addition, the axis of rotation about each of pins 22, 22', 22" and 22'" is oriented approximately spatially parallel to the axis of rotation about that one pins 21, 21', 21" and 21'" rotatably connecting the corresponding one of output shafts 15", 16", 17" and 18" to the same pivoting link.

Typically, there will be used either a bearing set or a bushing arrangement between pivoting links 20, 20', 20" and 20'" and each of pins 21, 21', 21" and 21'" and pins 22, 22', 22" and 22'". Such bearing sets could be precision ground duplex pair bearings for a very high quality rotary coupling, or more cheaply, a lower quality needle bearing and thrust washer arrangement. Alternatively, self lubricating bronze or fiber glass bushings could be used in some situations. Another possibility in some situations would be the use of steel pins with polymeric pivoting links.

The lower plurality of pivoting links 20, 20', 20" and 20'", in addition to each having an end thereof being rotatably connected to base support 12 as described above, also each have the opposite end thereof rotatably connected by four further pins, 24, 24', 24" and 24'", to a corresponding one of four individual and separate hinged pivot holders, 25, 25', 25" and 25'", serving as link end constrainers and which have no direct connections therebetween. Each of these hinged pivot holders is formed as a two extended arms hinge rotatably connected to one another by a corresponding one of a set of pins, 26, 26', 26" and 26'", with the lower extended arm of each rotatably connected to its corresponding one of pivoting links 20, 20', 20" and 20'" by the its corresponding one of pins 24, 24', 24" and 24'". The relatively long, single column arms in each of hinged pivot holders 25, 25', 25" and 25'", and therefore relatively shorter lengths of the two curved column arms of pivoting links 20, 20', 20" and 20'" (and similarly of the upper plurality of pivoting links to be described below), allows the output structure to be described below to have greater ranges of angular motion because of at least reducing interference possibilities between them during angular deployments. Other geometrical shapes could be used. Pin set 24, 24', 24" and 24'", and pin set 26, 26', 26" and 26'", can again be used with bearing or bushing arrangements.

The axis of rotation of the lower arm connected to a corresponding one of the lower plurality of pivoting links 20, 20', 20" and 20'", in being able to rotate about its one of pins 24, 24', 24" and 24'", is directed so as to be more or less parallel to the length of the link and to the length of that upper arm of the corresponding one of hinged pivot holders 25, 25', 25" and 25'". The axis of rotation of each of links 20, 20', 20" and 20'" about a corresponding one of pins 22, 22', 22" and 22'", in being rotatably coupled to base support 12, and the rotation axis of the corresponding lower arm about the pin rotatably connecting it thereto are, in each link instance, perpendicular to planes that intersect one another at substantially right angles. These rotation axes for each of these links and its corresponding rotatably connected lower arm are also oriented in directions differing from those in an adjacent link, i.e. the next link thereafter around base support 12. This allows hinged pivot holders 25, 25', 25" and 25'" to be moved by the corresponding pivoting links substantially with respect to base support 12, but for the same length links these pivot holders will always be in a plane common thereto.

Manipulator 10 is shown in these figures having a further upper plurality of pivoting links. A corresponding one of this plurality is rotatably coupled to the upper arm of each of hinged pivot holders 25, 25', 25" and 25'" by a corresponding one of a further set of pins, 27, 27', 27" and 27'". The axis of rotation of the upper arm connected to a corresponding one of this upper plurality of pivoting links, in being able to rotate about its one of pins 27, 27', 27" and 27'", is directed so as to be more or less parallel to the length of the link and to the length of that upper arm of the corresponding one of hinged pivot holders 25, 25', 25" and 25'". As a result, there is a corresponding one of a set of angles, 28, 28', 28" and 28'", of a selectable angular magnitude between the axis of rotation of the lower arm in a hinged pivot holder rotatably connected to a pivoting link from the lower plurality thereof and the axis of rotation of the upper arm in that hinged pivot holder rotatably connected to the corresponding one of the upper plurality of pivoting links as shown in these figures, i.e. between the upper and lower arms of each hinged pivot holder. The selection of the magnitude of each of angles 28, 28', 28" and 28'" is accomplished by the degree of extension of output shafts 15", 16", 17" and 18" of linear actuators, 15, 16, 17 and 18 outward from bases 15', 16', 17' and 18' thereof, and affects the capabilities of manipulator 10 as will be described below.

Another set of pins, 29, 29', 29" and 29'", are each used at the opposite end of a corresponding one of the above mentioned upper plurality of pivoting links, 30, 30', 30" and 30'", to rotatably connect them to an output structure. If manipulator 10 is constructed symmetrically above and below a plane including the axes of radial symmetry of each of hinged pivot holders 25, 25', 25" and 25'", i.e., angles 28, 28', 28" and 28'" in these figures being bisected by such a common plane, the upper plurality of pivoting links 30, 30', 30" and 30'" can be identical in construction with each other and with each of the lower plurality of pivoting links 20, 20', 20" and 20'". Although this is a significant economic factor in manufacturing significant numbers of joint or manipulator 10, this symmetry is not required for successful operation of such manipulators. Also, the lengths of pivoting links in the upper and lower pluralities thereof need not all be the same to have successful operation of manipulator 10 but the pattern of the positioning of this output structure will change depending on such differences.

The output structure which is controlled in manipulator 10 by motion of output shafts 15", 16", 17" and 18" of linear actuators, 15, 16, 17 and 18 has a hole, 31, provided therethrough in a symmetrical cruciform shaped spider support structure, or manipulable support, 32. Again, geometrical shapes other than such a spider support structure can be used, and again various items can be extended through opening 31 such as electrical wiring or optical fibers or, in this output situation, a further mechanical device supported on support 32, or some combination of such features or other alternatives. Each of pivoting links 30, 30', 30" and 30'" in the upper plurality thereof is rotatably coupled by a corresponding one of pins 29, 29', 29" and 29'" to an arm of the spider support structure of manipulable support 32. Here too, each of pins 29, 29', 29" and 29'" is affixed to an arm of support 32 such that the corresponding one of the plurality of upper pivoting links rotatably coupled to manipulable support 32 thereby rotates about an axis therethrough that is oriented perpendicular to a radius extending outward from the center of the spider support structure of manipulable support 32 through that arm to which it is affixed. Although the rotation axes of the pivoting links at the rotary couplings thereof to supports 12 and 32 are described as making equal angles with adjacent ones thereof as they occur about those supports, these angles need not be identical about either support, nor identical about one support with those about the other, to be able to position support 32 over a substantial angular range, though providing substantially such identities is often convenient.

The axis of rotation of such a one of pivoting links 30, 30', 30" and 30'" in the upper plurality thereof about its pin coupling it to support 32 extends through that pin more or less perpendicular to the direction of the length of that link, and substantially parallel to the axis of rotation about the pin rotatably coupling the corresponding one of pivoting links 20, 20', 20" and 20'" in the lower plurality thereof to base support 12 when manipulable support 32 is vertical. The correspondence here between upper and lower plurality pivoting links is established by each being coupled to the same one of hinged pivot holders 25, 25', 25" and 25'". Again here, as for links in the lower plurality thereof, the axis of rotation of each of links 30, 30', 30" or 30'" in the upper plurality thereof about its corresponding one of pins 29, 29', 29" or 29'", in being rotatably coupled to a corresponding arm of the spider support structure of manipulable support 32, and the rotation axis of the corresponding upper arm about the one of pins 27, 27', 27" or 27'" rotatably connecting it thereto are, in each link instance, perpendicular to planes that intersect one another at substantially right angles.

Figure 5:
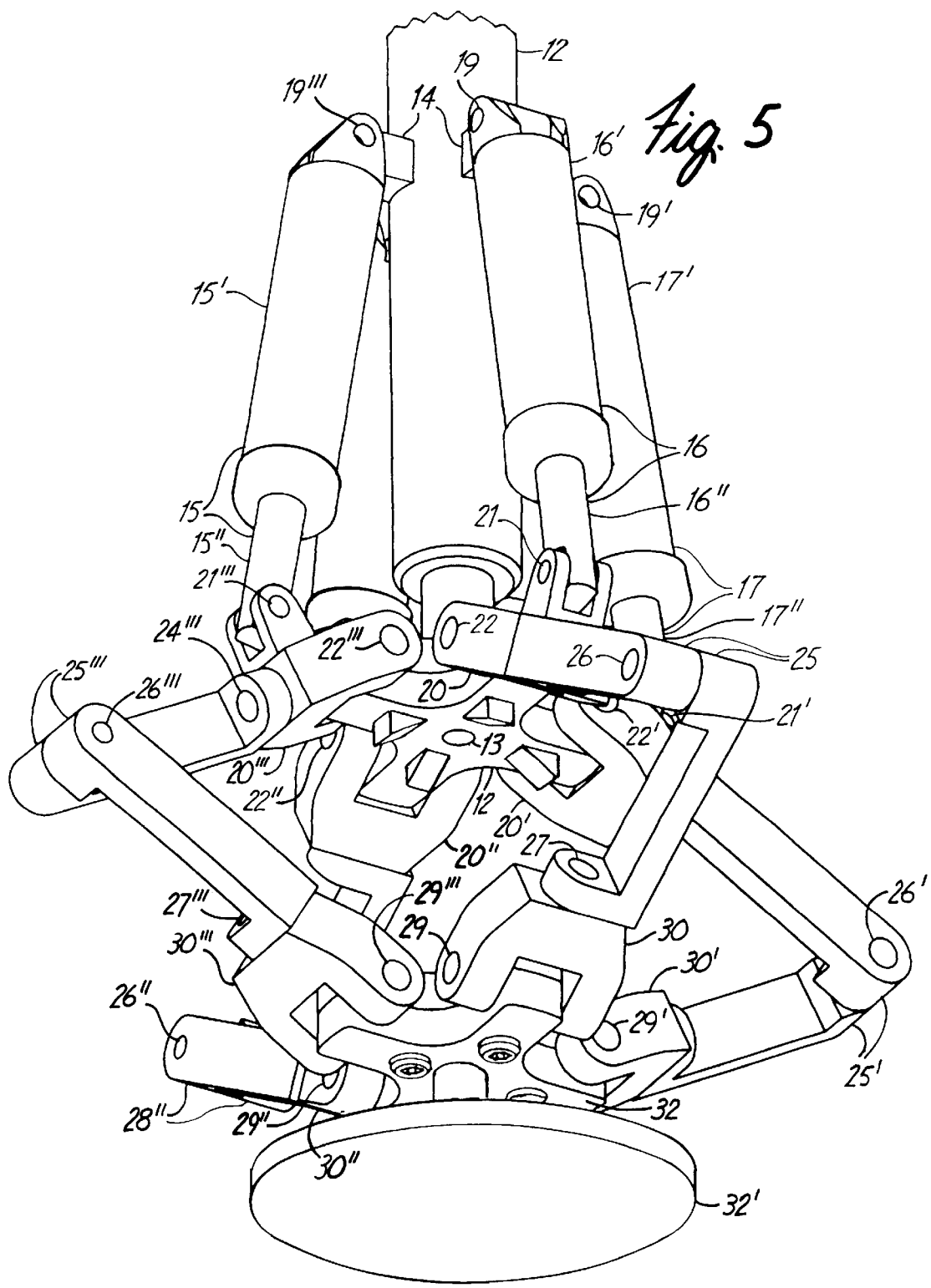

Manipulator 10 can be changed in function from being a controlled manipulator by making changes with respect linear actuators 15, 16, 17 and 18. If they are replaced with shock absorbers, a shock impact absorber can be made for reducing shock magnitudes upon impacting surfaces, even surfaces of uneven topography. Such a shock absorber would be useful, for instance, as a landing foot for a vertical flight machine such as a landing vehicle from a spacecraft. Such an arrangement is shown in FIG. 5 which shows more or less the structure of FIG. 1 inverted in position with base 11 remove, and with linear actuators 15, 16, 17 and 18 now replaced with corresponding shock absorbers in connection with which the same numerical designations have been retained as they have for structures having the same purpose as similar purpose components in the joints or manipulator examples previously given.

In addition, manipulable support 32 has an impact plate, 32', affixed thereto in opening 31. A substantial impact of impact plate 32' on an uneven or canted surface will cause plate 32' to rotate on the hinged member connected lower and upper pluralities of pivoting links 20, 20', 20" and 20'" and 30, 30', 30" and 30'", and to experience a partially vertical force, a force leading to forces in these connected links that will be at least partially absorbed in shock absorbers 15, 16, 17 and 18. Such absorption will reduce the shock to whatever is chosen to be supported on support 12 during the impact.

Figure 6:
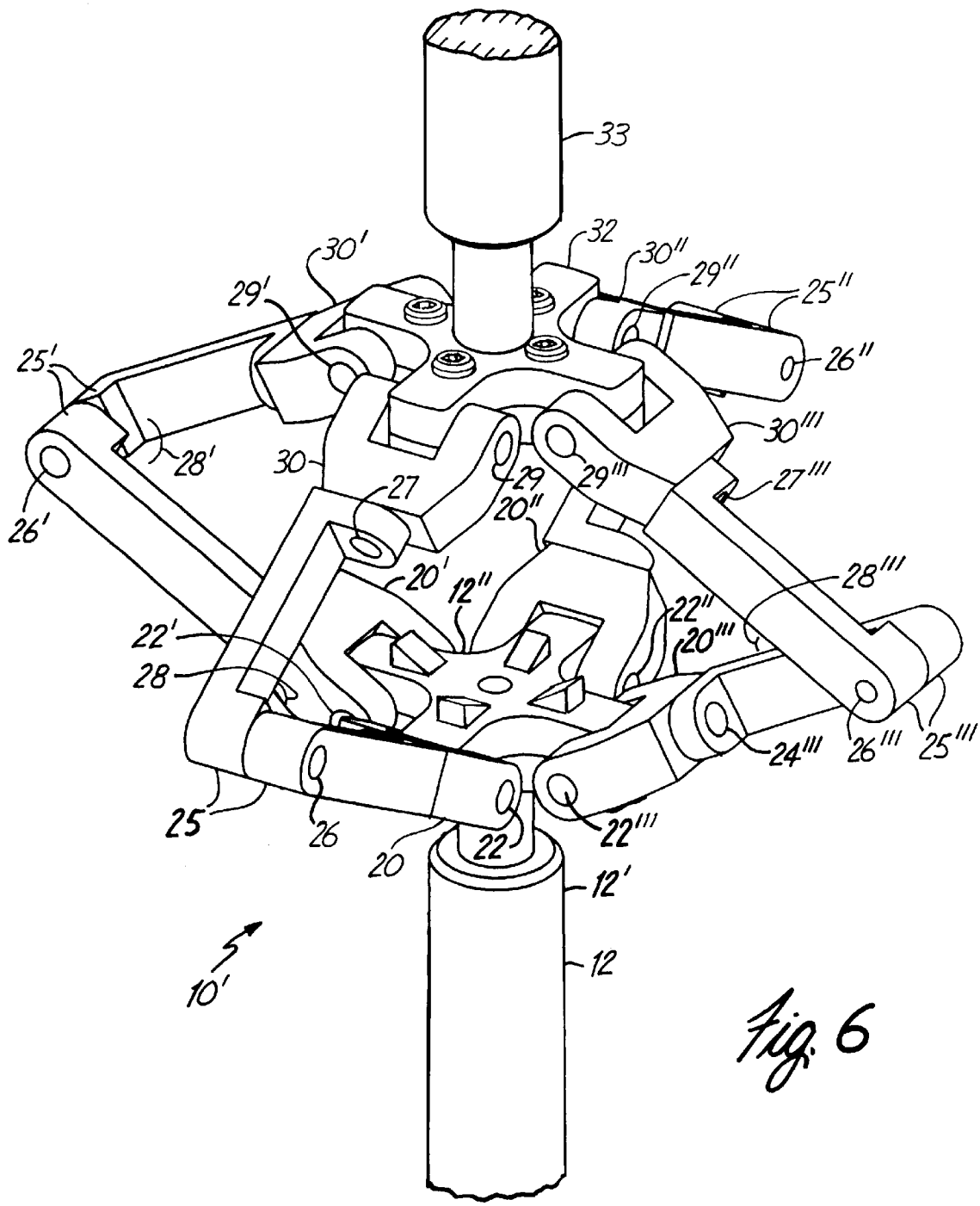

If linear actuators 15, 16, 17 and 18 are removed altogether from the corresponding ones of the lower plurality of pivoting links 20, 20', 20" and 20'" by removing corresponding screws 21 and 21', joint or manipulator 10 would no longer be capable of being operated to position manipulable support 32 at a desired position or serve as a shock absorber. However, in these circumstances, should the rotational driving system involving drive a shaft and pinion gear 11' for rotating mounting arrangement 11 be activated, or alternatively should mounting arrangement 11 or some variant thereof or just base support 12 be rotated in some other fashion, the system shown in FIGS. 1, 2 and 3 will operate as a flexible joint with manipulable support 32 following the rotation of mounting arrangement 11 and base support 12 to transmit that rotational motion to manipulable support 32 without requiring supports 12 and 32 to be axially aligned, i.e., the axis of radial symmetry of one can be at a substantial angle with respect to the radially symmetrical axis of the other. A constant velocity joint performance can be achieved with such an arrangement, an example of which is shown in FIG. 6 as joint 10' having an output shaft, 33, affixed to manipulable support 32. In this figure, too, structures having the same purpose as similar purpose components in the joints or manipulator examples previously given have retained the same numerical designations here as were used in the earlier examples.

The various structural components of joint or manipulator 10 described in connection with FIGS. 1 through 4 above are typically formed of a metal or metals, or alloys thereof, appropriate for the intended use, i.e. perhaps stainless steel for a medical use, aluminum or titanium where weight is a primary concern, etc. Many or all of these components could molded polymeric materials instead.

If each of linear actuators 15, 16, 17 and 18 extends its corresponding output shaft 15", 16", 17" and 18" outwardly, each such extension will cause the lower pivoting link connected thereto to also rotate in an upward, or clockwise, direction to lift the opposite end thereof connected to a hinged pivot holder upward away from base 11 and toward the axis of rotational symmetry of base support 12, i.e. the vertical direction, with the result seen in FIG. 4. In turn, the lower arm of the hinged pivot holder rotatably connected to each of these lower pivoting links is forced to rotate in one direction about the hinge pin that rotatably connects it to the upper arm of that hinged pivot holder. The accompanying inward motion of the lower pivoting link end and the connected lower arm of the hinged pivot holder forces the upper arm of that holder rotatably connected to a corresponding upper pivoting link to rotate in an opposite direction about this hinge pin and forces this latter link upward as the angle between the two arms increases. That is, such rotations by these linear actuators of the lower pivoting links that are matched both in angular extent and direction results in moving manipulable support 32 away from base support 12 along the axis of radial symmetry of manipulable support 32. Conversely, if the output shafts of each of these linear actuators retracts inwardly to a matched extent, manipulable support 32 will be moved toward base support 12 along the radial axis of symmetry of that support as the angles between the arms of the hinged pivot holders decrease.

On the other hand, matched output shaft extensions and retractions of the members of a pair of linear actuators positioned on opposite sides of base support 12 across from one another, without movement of the output shafts of the other pair of linear actuators, will result in tilting manipulable support 32 toward the direction of the linear actuator that is retracting which will eventually bring this support directly over this retracting actuator. Adding output shaft extension to the previously unmoving output shafts of the other pair of linear actuators will allow a significant increase in the tilt angle achieved but can reduce extension of manipulable support 32 along its axis of radial symmetry at some point because the hinged pivot holder connected to the initially extending actuator output shaft reaches its rotational limit.

Matched output shaft extensions and retractions in opposite directions of the members of both pairs of linear actuators positioned on opposite sides of base support 12 across from one another will result in tilting manipulable support 32 toward a direction halfway between the linear actuators in the pairs that are retracting in a downward direction again with limited extension of manipulable support 32 along its axis of radial symmetry. Such retractions which are unmatched in magnitude will result in tilting manipulable support 32 toward a direction between the linear actuators in the pairs that are retracting that is closer to the one having the output shaft that retracts over the larger distance. The various tilts described above of manipulable support 32 from the vertical will be further described below. Of course, combined tilting motions and extension or contraction motions of manipulable support 32 along its axis of radial symmetry can be provided by suitable retractions and extensions of the output shafts of these linear actuators in selected directions and amounts.

Two views of joint or manipulator 10 of FIG. 1 are shown in FIGS. 2 and 3, each view showing a different, though extreme, tilt angle achieved by manipulable support 32. A smaller tilt angle situation for support 32, not shown, in which it is tilted to approximately 45° from the vertical extended over one of the linear actuators, allows this support to extend outward relatively far from base support 12. This result can be achieved by having output shaft 16" of linear actuator 16 retract the lower pivoting link connected thereto downward while output shafts 15", 17" and 18" of linear actuators 15, 17 and 18 each extend to rotate the one of lower pivoting links 20'", 20" and 20' connected thereto in an upward direction with the greatest extension provided by output shaft 18" of linear actuator 18. If output shaft 18" of linear actuator 18 extends to rotate lower pivoting link 20" to nearly a vertical position with output shafts 15" and 17" of linear actuators 15 and 17 each extending the lower pivoting link connected thereto upward to a relatively small angle, and with output shaft 16" of linear actuator 16 retracting the lower pivoting link connected thereto downward to a relatively small angle, manipulable support 32 will extend a modest distance outward along its axis of rotational symmetry at this tilt angle. If, instead, output shaft 18" of linear actuator 18 extends to rotate lower pivoting link 20" to nearly a vertical position but with output shafts 15" and 17" of linear actuators 15 and 17 each now extending the lower pivoting link connected thereto upward to a relatively great angle, and with output shaft 16" of linear actuator 16 still retracting the lower pivoting link connected thereto downward to a relatively small angle, manipulable support 32 can achieve this same tilt angle but with much greater extension outward along its axis of rotational symmetry.

FIG. 2 shows manipulable support 32 rotated to something more than 90° from the vertical over linear actuator 16. This is achieved by output shaft 18" of linear actuator 18 extending to rotate lower pivoting link 20" to approximately a vertical position. Output shafts 15" and 17" of linear actuators 15 and 17 each extend the lower pivoting link connected thereto upward to a relatively small angle, and output shaft 16" of linear actuator 16 retracts the lower pivoting link connected thereto downward to a relatively small angle.

The situation in FIG. 3 has manipulable support 32 rotated to something more than 90° from the vertical along a vertical plane which is oriented at about 45° from each of linear actuators 15 and 16. This result comes about by output shafts 17" and 18" of linear actuators 17 and 18 having extended to rotate lower pivoting links 20' and 20", respectively, to approximately a vertical position with output shafts 15" and 16" of linear actuators 15 and 16 correspondingly having extended to rotate lower pivoting links 20' and 20'" to a below horizontal position.

Other azimuthal angle positions with respect to base support 12, along with selected angular deviations from vertical, can be provided for manipulable support 32 by corresponding combinations of direction and amount of rotation of each of linear actuators 15, 16, 17 and 18. Here again, although the separation of manipulable support 32 from base support 12 can be significantly increased when the axis of rotational symmetry of manipulable support 32 is aligned with, or at relatively small angles with respect to, the axis of rotational symmetry of base support 12, the possibility of such a separation increase between these supports is reduced as the tilt angle of support 32 increases from the aligned position to significantly larger angular deviation values because of the occurrence of interference between the pivoting links.

The capability of joint or manipulator 10 set out in FIGS. 1 through 4 to move precisely not only over a spatial surface defined by the range of tilt angles available to manipulable support 32, but also angularly over different spatial surfaces offset from one another in radial directions with respect to base support 12 (at least at angles from the vertical not too far from the vertical) provides an instrument capable of intricate actions at its output end, that is, at manipulable support 32. Uses for such an instrument might include assembling components into an assembly, altering surfaces of materials through various kinds of surface geometry or texture changing activities, or performing surgical procedures.

Figure 7:
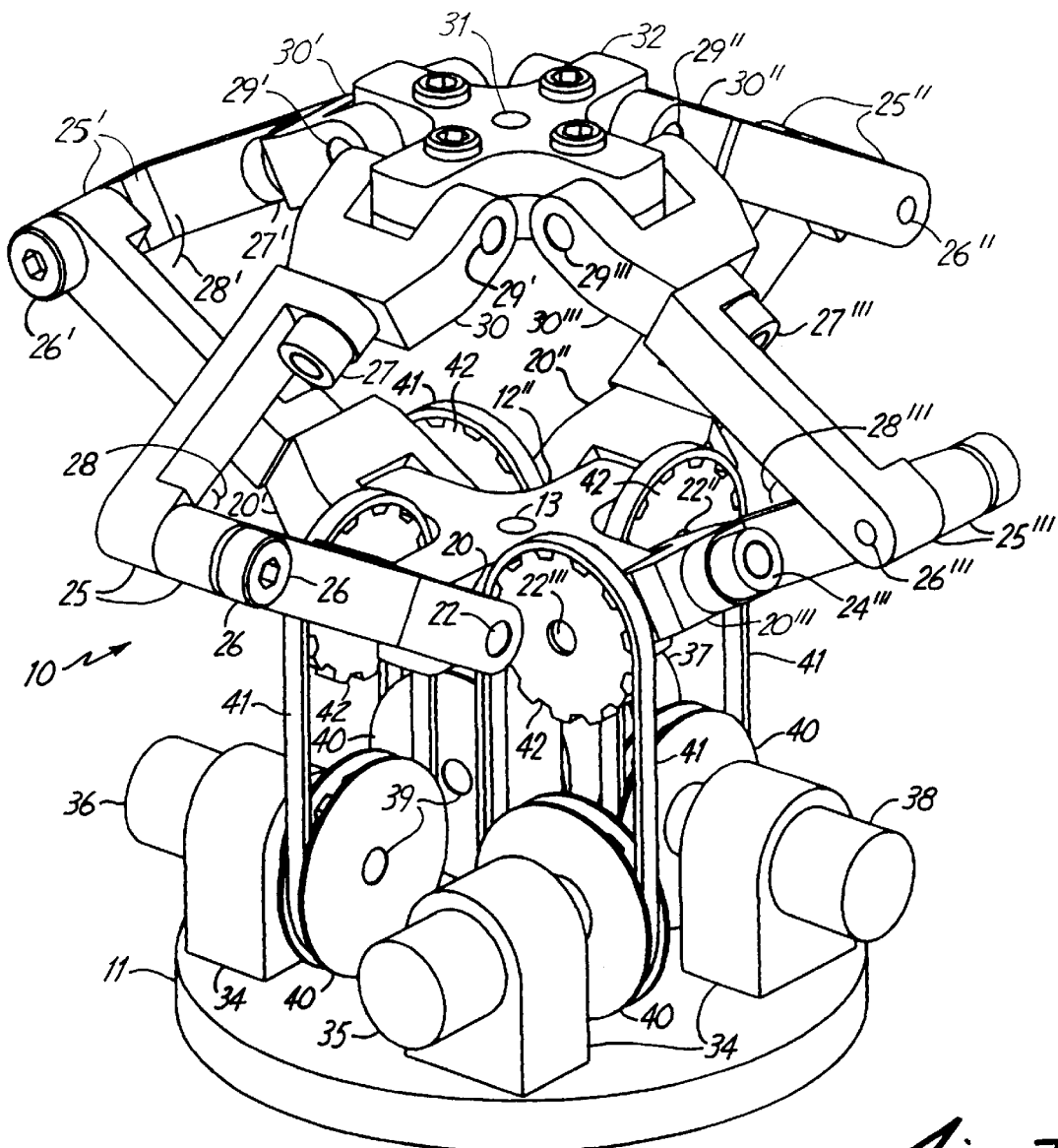

Other drive systems can be used in place of linear actuators 15, 16, 17 and 18. Alternatively shown in FIG. 7 are four rotary actuator support pedestals, 34, supported directly on mounting arrangement 11. Each is shown supporting an electric motor therein along with a belt and toothed pulleys interconnection arrangement between the rotor shaft of that electric motor and the remaining portions of manipulator 10. That is, four electric motors, 35, 36, 37 and 38, are each mounted in the corresponding one of pedestals 34, and each has an output shaft, or rotor, 39, on which is mounted a drive toothed pulley, 40. A toothed drive belt, 41, is engaged therearound and around a driven toothed pulley, 42, to complete each belt and toothed pulleys interconnection arrangement. Electric motors 35, 36, 37 and 38 each drive one of driven pulleys 42 that is rigidly affixed to the corresponding one of lower pivoting links 20, 20', 20" and 20'" concentrically about the one of pins 22, 22', 22" and 22'" therethrough (some of the other pins shown in FIG. 7 are alternatively shown as being capped on one end).

Rotation by the rotors in electric motors 35, 36, 37 and 38, clockwise or counterclockwise, causes drive pulleys 40 to rotate similarly. This rotation transmitted through the drive belt 41 thereabout to the associated driven pulley 42 further causes its one of pivoting links 20, 20', 20" and 20'" to in turn rotate one way or the other about the corresponding one of pins 22, 22', 22" and 22'".

Figure 8:
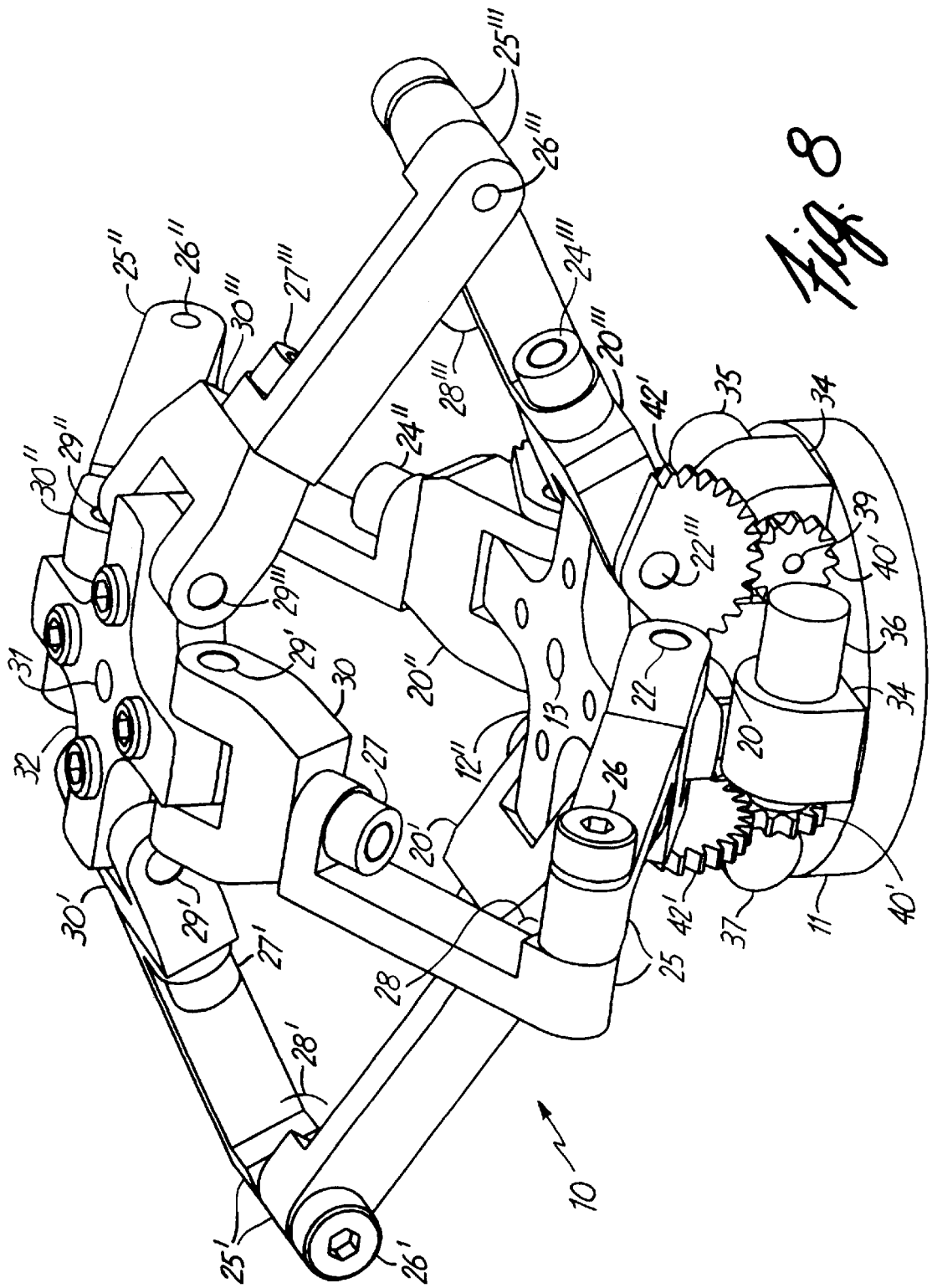

A further configurational alternative for joint or manipulator 10 is shown in FIG. 8 by the substitution of a motor driven, gear based drive train for directing motion of the pivoting links in the lower plurality thereof through the direct connection of electric motors 35, 36, 37 and 38 to these links for that purpose. This is accomplished by eliminating belts 41 and replacing pulley pairs 40 and 42 by a spur gear and spur gear sector pair, 40' and 42' of FIG. 7. (In each of these figures, structures having the same purpose as similar purpose components in the joints or manipulator examples previously given have retained the same numerical designations here as were used in the earlier examples.) Each of drive spur gears 40' is on a corresponding one of rotors 39, and each of spur gear sectors 42' is affixed to a corresponding one of the plurality of lower pivoting links concentrically about the one of 22, 22', 22" and 22'" therethrough (here too, some of the other pins are shown having an end with a cap). Again, rotation of the rotors 39 causes, through a gear 40' and gear sector 42" pair, rotation of the corresponding one of the lower pivoting links.

Figure 9:
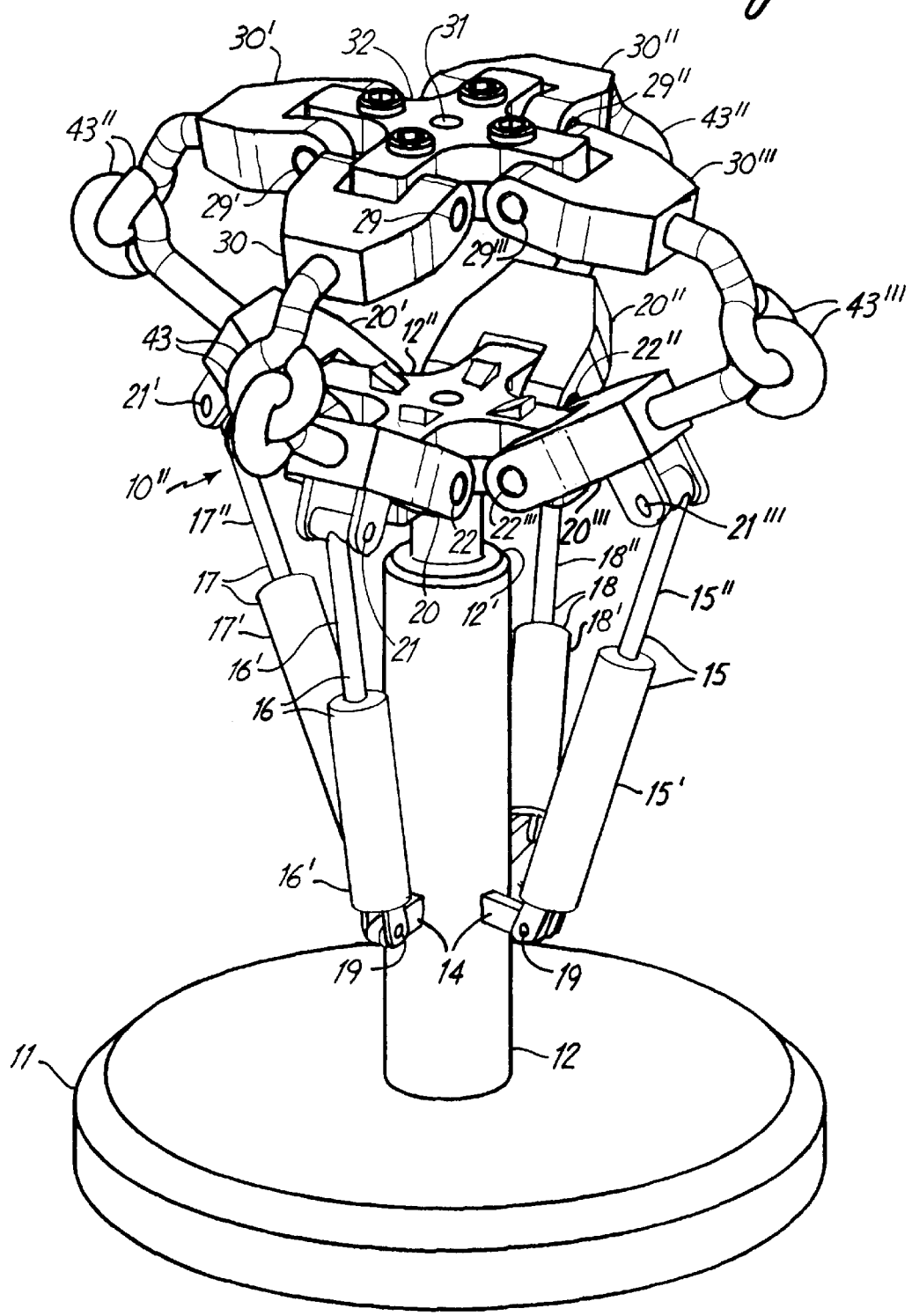
FIG. 9 shows a perspective view of an alternative embodiment of the present invention.

There are other possibilities for link end constrainers beyond hinged pivot holders 25, 25', 25" and 25'" for rotatably connecting each member of the lower plurality of pivoting links 20, 20', 20" and 20'" to a corresponding member of the upper plurality of pivoting links 30, 30', 30" and 30'". Pin set 26, 26', 26" and 26'" can be eliminated by the use of interconnected stemmed ring pairs, 43, 43', 43" and 43'", much like closed "eye" bolts, in place of hinged pivot holders 25, 25', 25" and 25'" as shown in manipulator 10" of FIG. 9, where again structures having the same purpose as similar purpose components in the joints or manipulator examples previously given have retained the same numerical designations.

Each interconnected stemmed ring pair has one of its ends opposite the interconnected rings fixedly inserted in a corresponding one of the lower plurality of pivoting links 20, 20', 20" and 20'" and the other, opposite end fixedly inserted in a corresponding one of the upper plurality of pivoting links 30, 30', 30" and 30'" to thereby rotatably join those lower and upper links. The interconnected rings, having the ring portion of the one extending through the ring or "eye" opening of the other, move with respect to one another much as if they were hinged together and rotatably connected to the corresponding ones of these coupled links. That is, the ring portion of the one extending through the "eye" opening of the other can "rotate" in that opening about a portion of the ring of the other extending through its own "eye" opening, and vice verse, to thereby allow one ring to move more or less in pitch and yaw motions with respect to support 12, and so to rotation of one with respect to the other about two different axes. In addition, some twisting motion of one ring with respect to the other can occur about a further and different axis to provide the needed added degree of freedom to allow achieving the desired manipulations of manipulable support 32. Such an arrangement can be made relatively cheaply and rugged.

Figure 10:
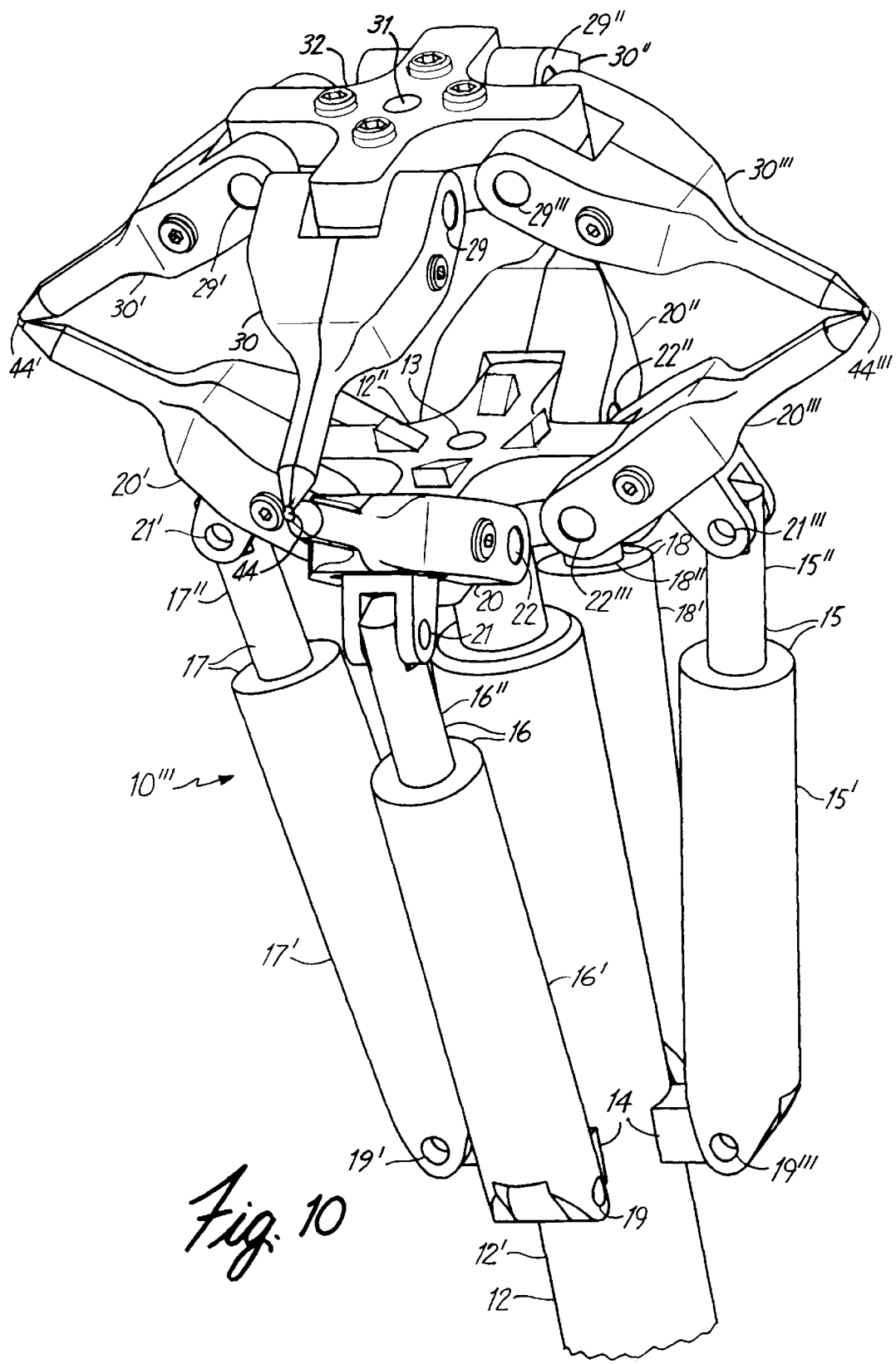
FIGS. 10 and 11 show perspective and a partial cross section side view of an alternative embodiment of the present invention.

As further alternative is shown in FIG. 10 where straps, 44, 44', 44" and 44"', such as cables or wires, are solely used as the "hinged" members in place of hinged pivot holders 25, 25', 25" and 25"' in forming link end constrainers to rotatably connect each member of the lower plurality of pivoting links 20, 20', 20" and 20"' to a corresponding member of the upper plurality of pivoting links 30, 30', 30" and 30"' in manipulator 10"'. The pitch and yaw motions, and the twisting motions, required of hinged pivot holders 25, 25', 25" and 25"' so that each member of the upper plurality of pivoting links 30, 30', 30" and 30"' can suitably move with respect to the corresponding member of the lower plurality of pivoting links 20, 20', 20" and 20"' to thereby permit manipulation of manipulable support 32 are all allowed by use of cables 44, 44', 44" and 44"'.

Figure 11:
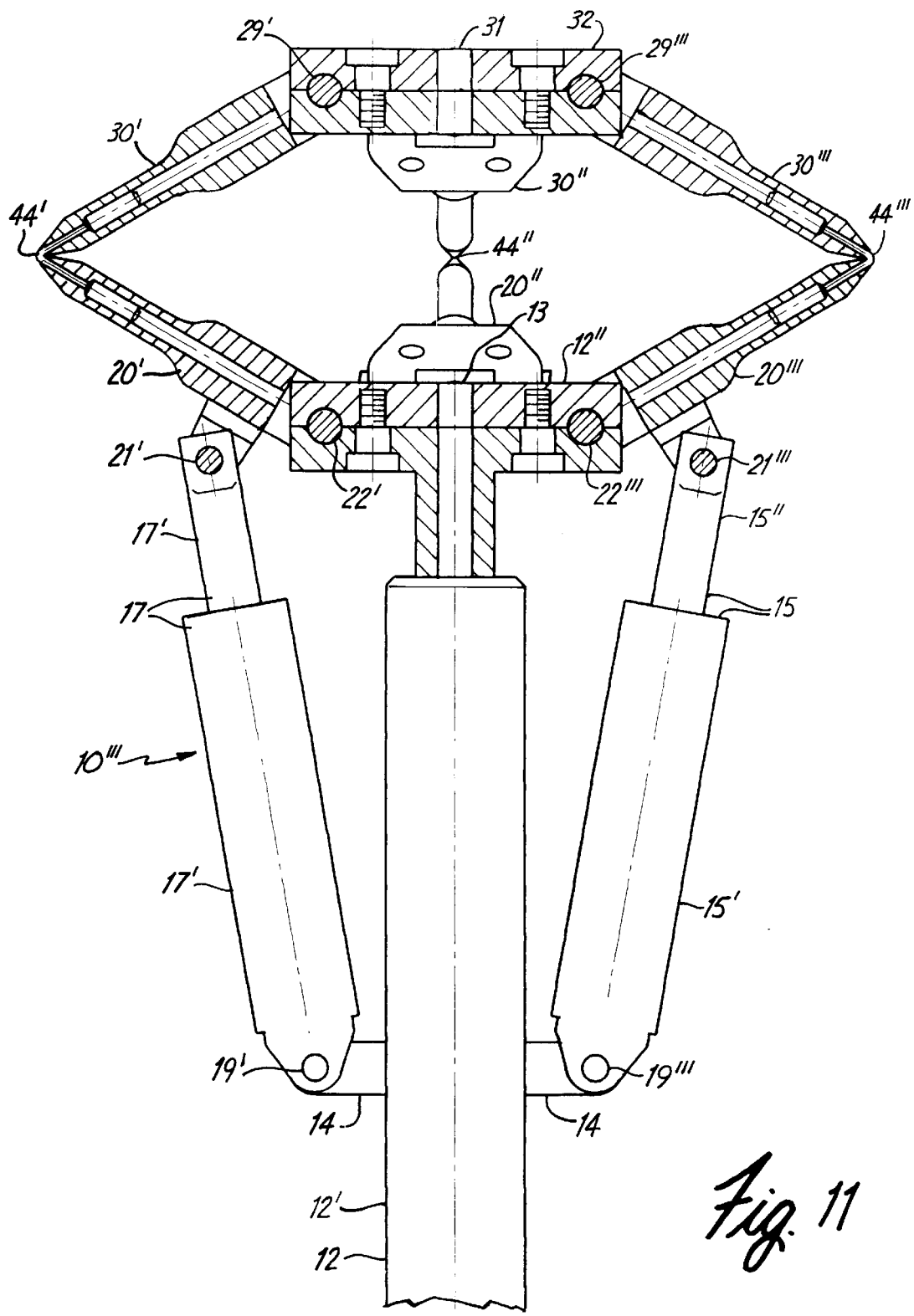

FIG. 11 shows both a partial cut away view and a partial cross section view of manipulator 10"' of FIG. 10. (As before, in these figures, structures having the same purpose as similar purpose components in the joints or manipulator examples previously given have retained the same numerical designations here as were used in the various earlier examples.) As can be seen there, each of cables 44, 44', 44" and 44"', a cable anchor is fastened to each end of each of these cables by crimping, soldering, welding, adhering or other suitable means. Each of the lower plurality of pivoting links 20, 20', 20" and 20"' and each of the upper plurality of pivoting links 30, 30', 30" and 30"' are provided in halves held together by some fastening means shown here to be a cap screw fitted through an opening in one half into a threaded opening in the other to fasten these halves together. Removing these cap screws allows these halves to be separated to accept the corresponding one of cables 44, 44', 44" and 44"' and its anchors therein, the halves being reassembled thereafter and fastened together again by the cap screws.

Figure 12:
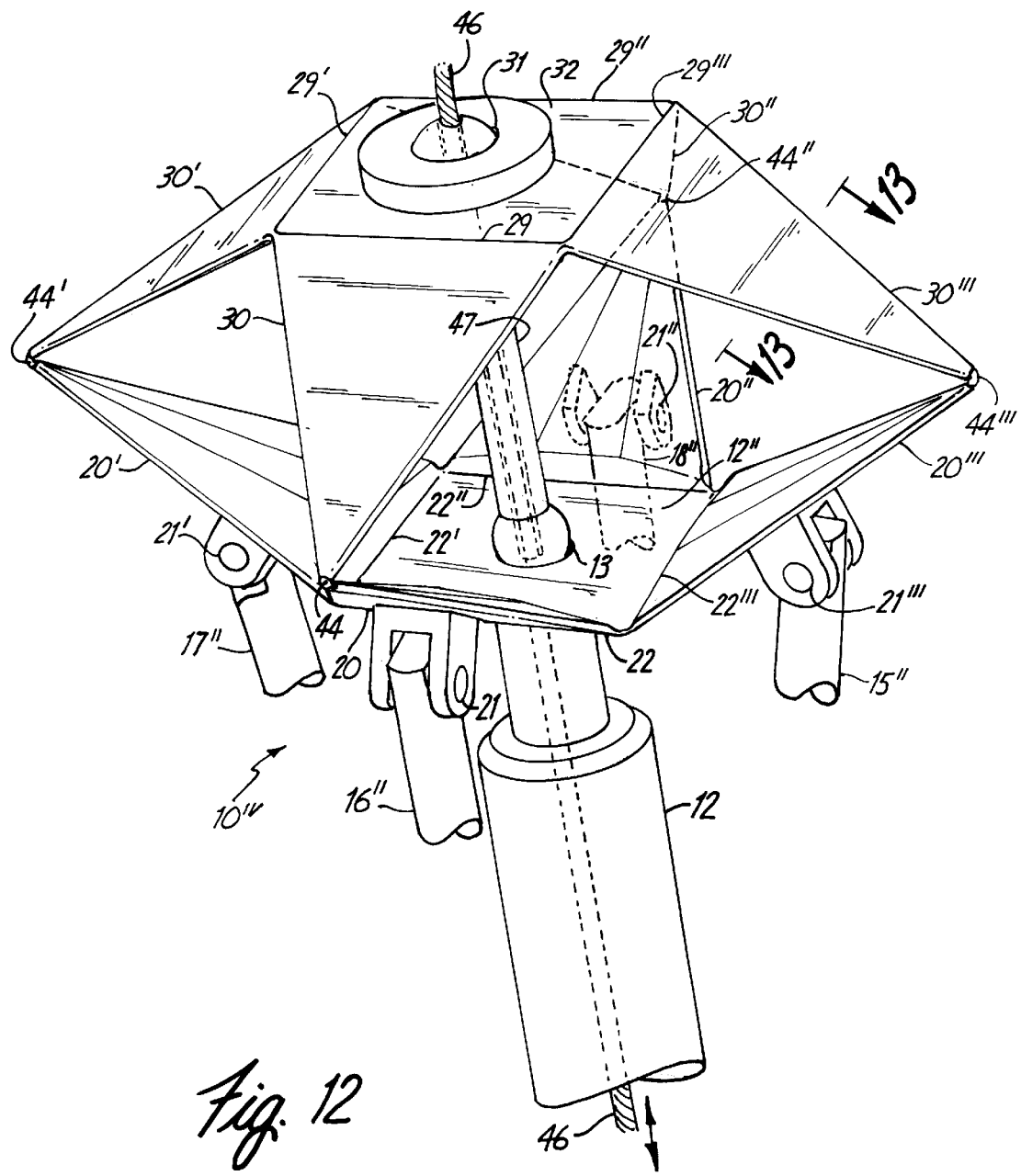
FIGS. 12 through 15 show perspective, cross section and top views of an alternative embodiment of the present invention.

The use of cables to connect corresponding members of the lower plurality of pivoting links 20, 20', 20" and 20"' and the upper plurality of pivoting links 30, 30', 30" and 30"' to allow pitch, yaw and twisting motions therebetween can be combined with molded plastic and "living hinges" to provide smaller, cheaper versions of manipulator 10"'. In a so called "living hinge", the two sides of the hinge are each integral with one of the two corresponding structural members being hinged together to accomplish the affixing of the hinge sides thereto, and the hinge pin is provided by a thinned portion of the material forming the hinge being continuously extended between these two corresponding structural members of thicker material rather than by a separate pin joining such members. A manipulator $10^{iv}$ version embodying such "living hinge" structures is shown in FIGS. 12, FIG. 12 being a perspective view. In these figures, structures having the same purpose as similar purpose components in the joints or manipulator examples previously given have retained the same numerical designations here as were used in the earlier examples. This is so even though there are significant structural differences in the structural members used in FIG. 12 as compared to similar purpose components used in the earlier examples because of the use of "living hinges" in the system of this figure in place of the pins or pivot screws used in the earlier examples.

Thus, output shaft 15" extending from linear actuator 15, not shown in FIG. 12 (having an opposite end thereof mounted on a mounting arrangement also not shown in this figure), is used to rotate pivoting link 20"' about "living hinge" 22"' that connects that pivoting link to base 12". In the same manner, output shaft 16" extending from linear actuator 16, not seen in this figure, is used to rotate pivoting link 20 about "living hinge" 22 connecting it to base 12". Again, output shaft 17" extending from linear actuator 17, not seen in this figure, is used to rotate pivoting link 20' about "living hinge" 22' connecting it to base 12". Finally, output shaft 18" (shown in dashed line form behind lower pivoting link 20") extending from linear actuator 18, not seen in this figure, is used to rotate pivoting link 20" about "living hinge" 22" connecting it to base 12". These "living hinges" replace corresponding pins 22"', 22, 22' and 22" in previous examples.

Similarly, pivoting link 30"' rotates about "living hinge" 29"' that connects that pivoting link to manipulable support 32, pivoting link 30 rotates about "living hinge" 29 that connects that pivoting link to support 32, pivoting ink 30' rotates about "living hinge" 29' that connects that pivoting link to support 32, and pivoting link 30" rotates about "living hinge" 29" that connects that pivoting link to support 32. These "living hinges" replace corresponding pins 29"', 29, 29' and 29" in previous examples Pivoting link 20"' is connected by cable 44"' to pivoting link 30"' which in turn rotates about "living hinge" 29"' that connects that pivoting link to manipulable support 32. Similarly, pivoting link 20 is connected by cable 44 to pivoting link 30 which in turn rotates about "living hinge" 29 that connects that pivoting link to manipulable support 32. Also in this manner, pivoting link 20' is connected by cable 44' to pivoting link 30' which in turn rotates about "living hinge" 29' that connects that pivoting link to manipulable support 32. Lastly, pivoting link 20" is connected by cable 44" to pivoting link 30" which in turn rotates about "living hinge" 29" that connects that pivoting link to manipulable support 32.

Figure 13:

As can be seen, pivoting links 20, 20', 20" and 20"' in the lower plurality thereof are each formed of a structural polymer or a metal in a triangular shape when viewed from the "top" thereof with the triangle base occurring at the "living hinge" between the link and base 12" commonly formed therewith. The link sides extend toward the opposite triangle apex that occurs where the corresponding cable emerges therefrom. In a "side" view, these same links are seen as extended wedge shapes with the thickest wedge portion formed at the "living hinge" part thereof, and with the link tapering in thickness from there to the point where the cable emerges therefrom. Pivoting links 30, 30', 30" and 30"' in the upper plurality thereof are provided in the same manner with manipulable support 32. A cross section view of pivoting link 30"' is shown in FIG. 13 as an example of the cross section of both upper pivoting links 30, 30', 30" and 30"' and lower pivoting links 20, 20', 20" and 20"'.

Hinged pivot holders 25, 25', 25" and 25"' are again provided as cables 44, 44', 44" and 44"' as in FIGS. 10 and 11, as indicated above, to form the couplings between the corresponding lower and upper link connections in FIG. 12 but in a different manner to be described below. Base 12" and manipulable support 32 are each provided as approximately square blocks with central openings 13 and 31, respectively, by ending these blocks interiorly in truncated cylindrical shell portions about those openings.

The resulting structure in FIG. 12 for manipulator $10^{iv}$ can be used to position manipulable support 32 therein anywhere over a wide angular range by forcing pivoting links 20, 20', 20" and 20"' to selected rotational positions about the corresponding portion of base 12" to which they are rotatably coupled by "living hinges" 22, 22', 22" and 22"', respectively. The performance of such a manipulator $10^{iv}$ can be made quite repeatable if the structural members, especially the "living hinges" used therein, are carefully made with materials exhibiting the same properties from batch to batch as well as carefully maintaining essentially identical dimensions from batch to batch in each unit made such as by use of precise laser cutting techniques. In addition, joint or manipulator $10^{iv}$ can be made exceedingly small by using these methods.

FIG. 12 also shows in addition the use of an operating strand, 46, often chosen to be a metal cable, extending through a tubular opening in support 12 merging into opening 13 in base 12", through a tubular opening in a separator sleeve arrangement, 47, and finally through opening 31 in manipulable support 32. Separator sleeve arrangement 47 has bulbous ends about the tubular opening extending therethrough to prevent those ends from passing through the corresponding one of openings 13 and 31 to result in sleeve arrangement being a manipulator $10^{iv}$ compression limiter setting a minimum distance between base 12" and manipulable support 32. Operating strand 46 is provided to operate some device connected to the end thereof extending past manipulable support 32, or alternatively is provided to be a conductive metal electrical interconnection lead for positioning, emplacing or mounting in or on a desired object or base.

Figure 14:
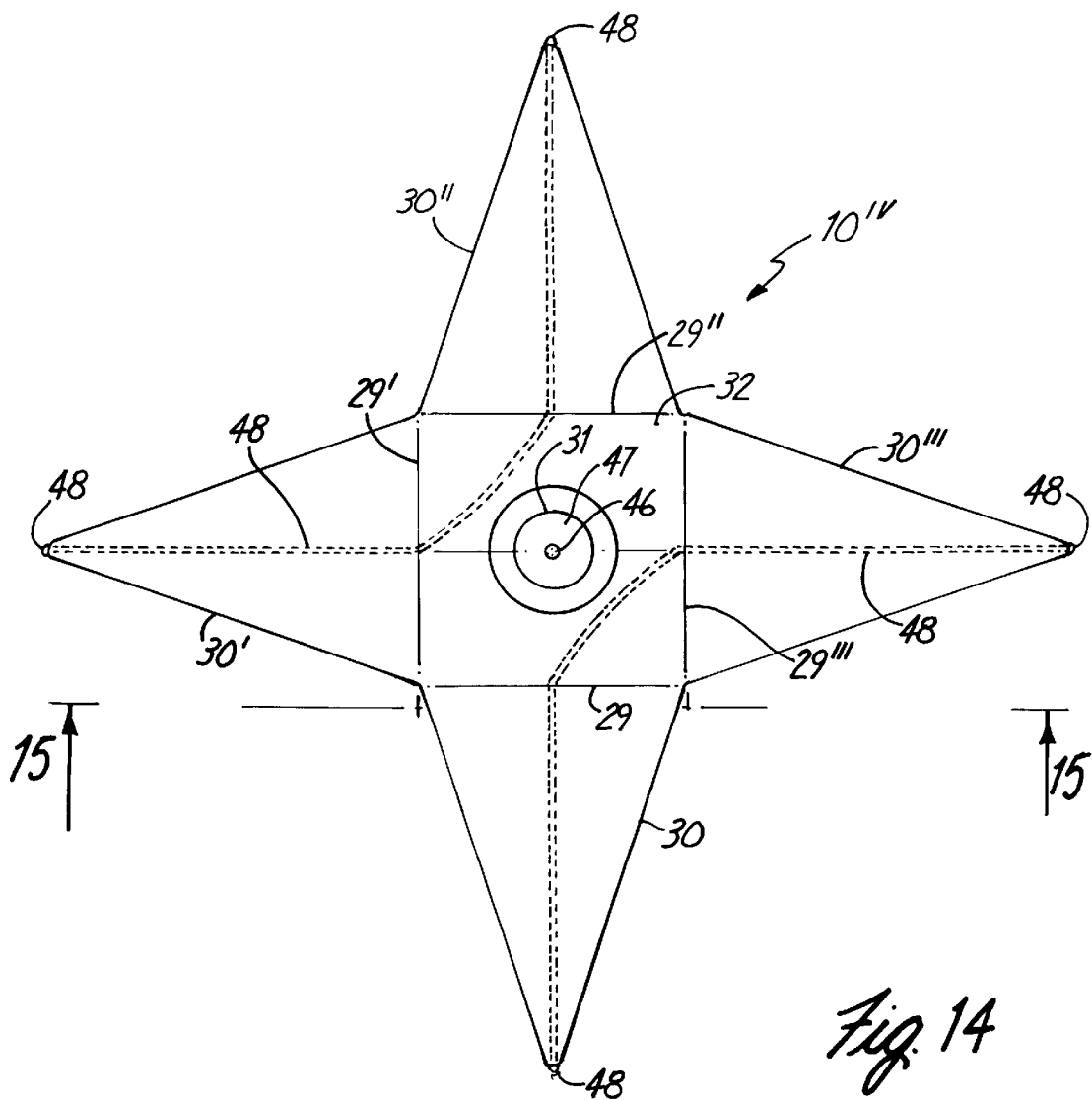

FIG. 14 shows another "living hinge" version with cables 44, 44', 44" and 44''' of FIGS. 10, 11 and 12 being provided by a single cable, 48, molded into the structural polymer material forming upper pivoting links 30, 30', 30" and 30''', lower pivoting links 20, 20', 20" and 20''', base 12" and manipulable support 32. In a typical arrangement, a "one shot" multicavity mold is provided have closed loop cable 48 appropriately suspended therein for injection molding of a "living hinge" manipulator $10^{iv}$ into which a structural polymer is injected such as polypropylene which may also have fibers distributed therein for strength such as fiber glass.

After such a fabrication molding, cable 48 can be seen in FIG. 14 to extend the length of upper pivoting link 30 from where it enters at the triangular apex from lower pivoting link 20 directly therebelow to bisect "living hinge" 29 and enter manipulable support 32. From there cable 48 extends across the corner of that manipulable support to the center of "living hinge" 29''' to then extend through upper pivoting link 30''' to the triangular apex thereof where it emerges to enter lower pivoting link 20''' directly therebelow at its triangular apex. Cable 48 then extends through link 20''' to bisect living hinge 22''' (not seen in this figure) and enter base 12" to extend across the corner thereof to the center of "living hinge" 22" (again not seen in this figure). Cable 48 then extends through lower pivoting link 20" to the triangular apex thereof (once more not seen in this figure) where it emerges to enter upper pivoting link 30" at its triangular apex. Cable 48 then follows a path through upper pivoting link 30", "living hinge" 29", manipulable support 32, "living hinge" 29', upper pivoting link 30', lower pivoting link 20', "living hinge" 22', base 12", "living hinge" 22 and lower pivoting link 20 to reach the triangular apex thereof and emerge to enter the triangular apex of link 30 on a path that mirrors the first half path described previously.

Figure 15:
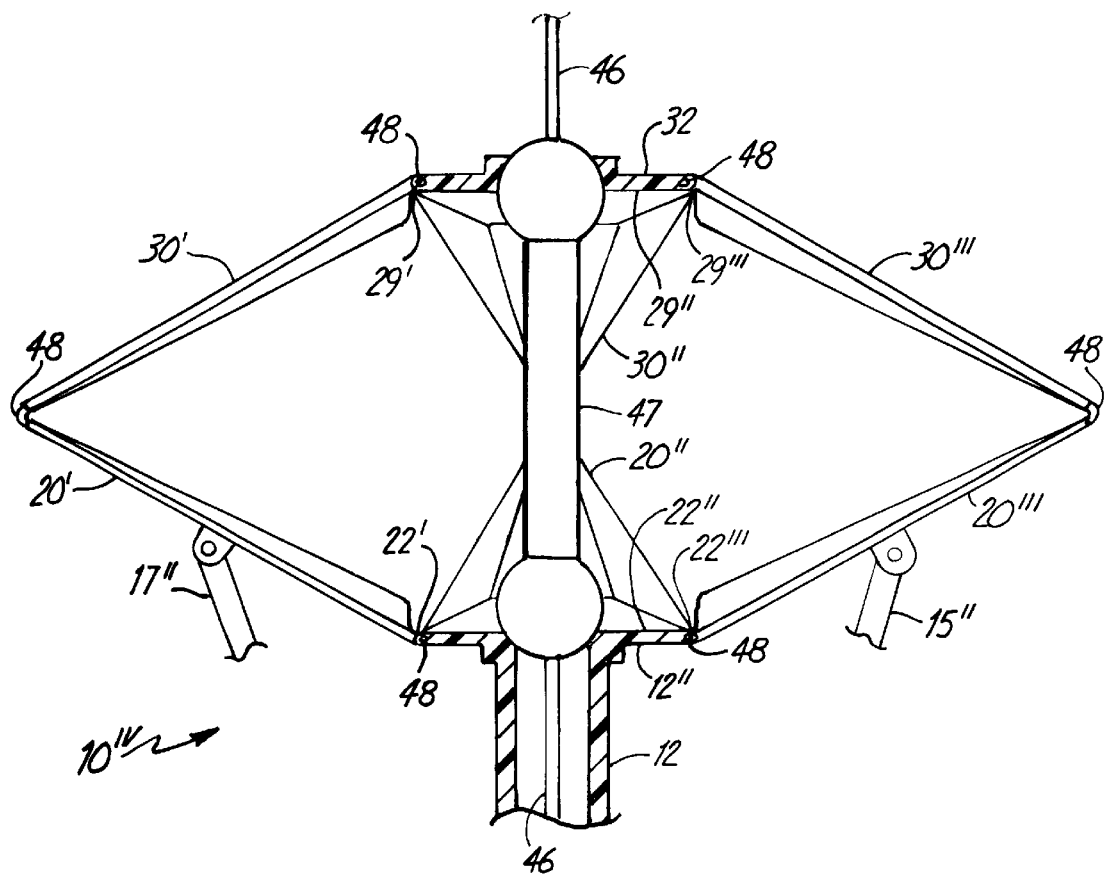

As indicated in FIG. 14, a broken section view of manipulator $10^{iv}$ of that figure is shown in FIG. 15. The section view in FIG. 14 is taken in line with "living hinge" 29 but is broken to be parallely crossing manipulable support 32 in the center thereof through strand 46. Cable 48 can be seen where positioned in base 12" and manipulable support 32 at the cross section.

In some situations, a more economical version of manipulator $10^{iv}$ can be provided by eliminating cable 48 from the structure and substituting in place thereof, at the locations where upper pivoting links 30, 30', 30" and 30''' were coupled to lower pivoting links 20, 20', 20" and 20''' thereby, further "living hinges" molded with the structural polymer material forming them. Again, polypropylene (possibly having distributed fibers therein) is typically used as the structural polymer and is injected into a multicavity mold this manipulator. Such an arrangement is shown for manipulator $10^{iv}$ in the perspective view of FIG. 16 and the fragmentary view of FIG. 17.

These further "living hinges", 49, 49', 49" and 49''', as the straps joining the triangular apexes of each corresponding pair of upper and lower pivoting links cannot be formed as a relatively wide, flat sheet-like portion of thinned polymer material, as are the "living hinges" replacing pins 22, 22', 22" and 22''' and pins 29, 29', 29" and 29''' described above. They must instead be more cable-like in form, as is shown in FIG. 17, to allow rotational motion in two different directions and sufficient twisting motion. Furthermore, the diameter or girth of these straps, and the nature of any filler distributed in the structural polymer must all be chosen to provided sufficient strength and durability for operation, but at the same time sufficient flexibility to allow easy execution of these motions.

The use of a multicavity mold to form this version of manipulator $10^{iv}$ in a single injection step without first having to suspend a cable in the mold reduces molding costs. If sufficiently cheap to manufacture, this version of manipulator $10^{iv}$ can be a one time, or few times, use device making it especially suitable for medical procedures. Of course, the cost of the version shown in FIG. 12 may also be sufficiently low in many instances for the same sort of uses.

FIGS. 18 and 19 show an arrangement for using one of the versions of manipulator $10^{iv}$ for attaching an electrical interconnection lead to a biological object such as a human heart for purposes of connecting a heart pacemaker thereto. FIG. 18 shows a right angle support plate, 50, supporting on its horizontal portion a housing, 51, both in dashed line form to avoid obscuring other structures present. Housing 51 has therein linear actuators 15, 16, 17 and 18 therein mounted on base support 12. The upright portion of plate 50 has a hole therein to accommodate a linear actuator output shaft length extender, 52. Extender 42 has five openings through the length thereof four of which have extended versions of output shafts 15', 16', 17' and 18' in the form of flexible, though stiff, wires positioned therein. The fifth long opening through extender 52 is occupied by strand, or interconnection lead, 46.

An extender sleeve, 53, connects the opposite end of extender 52 to manipulator $10^{iv}$ at base 12". Wire output shafts 15', 16', 17' and 18' are connected to lower pivoting links 20''', 20, 20' and 20", respectively, as before, through extender sleeve 53 limiting lateral motion thereof so that the wire shafts transmits all back and forth motion thereof at the opposite ends to these links. Extender sleeve 53 is omitted in the more detailed view of manipulator $10^{iv}$ in FIG. 19 for clarity.

Strand 46 extends through support 12, base 12" and manipulable support 32, and then through a square, relatively thin, stop, 54, before ending in a short helix, 55, with a sharpened lead point. Strand 46 can be rotated and translated along with the translation of manipulable support 32 by the linear actuators to screw helix 55 into the selected biological tissue. Alternatively, the whole of housing 51 and support plate 50 can be rotated and translated along with the translation of manipulable support 32 by the linear actuators to screw helix 55 into such selected biological tissue. This latter process requires that stop 54 be seated in the corresponding square opening in manipulable support 32 seen in FIG. 19 so that the rotating of manipulator 10$^{iv}$ forces stop 54, and so helix 55, to also rotate with the rotation of support plate 50, housing 51 and extender 52.

Although the present invention has been described with reference to preferred embodiments, workers skilled in the art will recognize that changes may be made in form and detail without departing from the spirit and scope of the invention.

What is claimed is:

1. A controlled relative motion system permitting a controlled motion member, joined to another base member, to selectively move with respect to that base member, said system comprising:

a base support;

a manipulable support;

a group of at least four link end constrainers each having a first portion movably connected to a second portion thereof such that ends of said first and second portions can be selectively separated from one another along a selected direction so as to have a selected distance therebetween;

a first group of at least four pivoting links each rotatably coupled to said base support so as to be rotatable about a corresponding base link axis and each coupled to a said first portion end of a corresponding one of said group of link end constrainers; and a second group of at least four pivoting links each rotatably coupled to said manipulable support so as to be rotatable about a corresponding support link axis and each coupled to a said second portion end of a corresponding one of said group of link end constrainers.

2. The apparatus of claim 1 wherein each of said first group of said pivoting links is rotatably coupled to said base support through use of a pin extending in said base support and that said pivoting link and about which rotation can occur by at least one of said base support and that said pivoting link.

3. The apparatus of claim 1 further comprising a first plurality of force imparting members each coupled to a said pivoting link in said first group thereof so as to be able to cause at least one of those said pivoting links in said first group thereof to rotate about its corresponding said base link axis, and wherein at least one of said first plurality of force imparting members provides a rotational motive force.

4. The apparatus of claim 1 further comprising a first plurality of force imparting members each coupled to a said pivoting link in said first group thereof so as to be able to cause at least one of those said pivoting links in said first group thereof to rotate about its corresponding said base link axis, and wherein at least one of said first plurality of force imparting members provides a linear motive force.

5. The apparatus of claim 1 further comprising a first plurality of constraining members each coupled to a said pivoting link in said first group thereof so as to be able to restrain at least one of those said pivoting links in said first group thereof in any rotation about its corresponding said base link axis.

6. The apparatus of claim 1 wherein said base support is held by a mounting arrangement.

7. The apparatus of claim 1 wherein each of said base link axes extend tangentially along a circular circumference of a corresponding circle centered in said base support, and each said base link axis being tangent to that said circle at a point separated from another such point adjacent thereto by an angle substantially equal to 360° divided by that total number of said pivoting links in said first group of pivoting links.

8. The apparatus of claim 1 wherein each of said first group of pivoting links is rotatably coupled to said first portion of a corresponding one of said group of link end constrainers so that said first portion is rotatable about a corresponding constrainer link axis, each of said first group of pivoting links having said corresponding base link axis thereof extending in a direction differing from that in which said corresponding constrainer link axis extends, each of said first group of pivoting links having said corresponding base link axis thereof and said corresponding constrainer link axis extending in different directions than do said corresponding base link axis and said corresponding constrainer link axis of another of said first group of pivoting links; and wherein each of said second group of pivoting links is rotatably coupled to said second portion of a corresponding one of said group of link end constrainers so that said second portion is rotatable about a corresponding constrainer link axis, each of said second group of pivoting links having said corresponding constrainer link axis extending in a direction differing from that in which said corresponding support link axis thereof extends, each of said second group of pivoting links having said corresponding constrainer link axis and said corresponding support link axis thereof extending in different directions than do said corresponding constrainer link axis and said corresponding support link axis of another of said second group of pivoting links.

9. The apparatus of claim 1 wherein each of said group of link end constrainers is provided as a bendable connecting strap with said first and second portions thereof each extending to a corresponding one of those said lower and upper groups of pivoting links coupled thereby.

10. The apparatus of claim 1 wherein each of said group of link end constrainers has said first and second portions thereof each provided as a stemmed ring closed about a ring opening with these rings passing through each other's ring opening, and with these stems each extending to a corresponding one of those said lower and upper groups of pivoting links coupled thereby.

11. The apparatus of claim 1 wherein each of said first group of pivoting links coupled to said base support is rotatably coupled to said base support through use of a hinge supported both by said base support and that said pivoting link.

12. The apparatus of claim 2 wherein at least one of said base support and said pivoting link between which said pin extends is coupled to said pin through a bearing means.

13. The apparatus of claim 2 wherein each of said first group of said pivoting links is rotatably coupled to said base support through use of a clevis formed in that said pivoting link.

14. The apparatus of claim 3 wherein each of said pivoting links in said first group thereof has coupled thereto a corresponding one of said first plurality of force imparting members.

15. The apparatus of claim 4 wherein each of said pivoting links in said first group thereof has coupled thereto a corresponding one of said first plurality of force imparting members.

16. The apparatus of claim 6 wherein said mounting arrangement comprises a base housing, said base housing comprising a plurality of force imparting members mounted therein each connected to a corresponding one of said first group of pivoting links.

17. The apparatus of claim 7 wherein each of said base link axes extend into regions between adjacent ones of said first group of pivoting links into which regions said base link axes of said adjacent ones also extend.

18. The apparatus of claim 8 where one of said first plurality of pivoting links has said base link axis thereof and said holding link axis thereof each oriented substantially perpendicular to planes which intersect one another at substantially right angles.

19. The apparatus of claim 11 wherein both said base support and said first group of pivoting links are formed from, and joined together by, a common material, and said hinge is formed at least in part by a thinned portion of that said material extending between said base support and each said pivoting link in said first group thereof.

20. The apparatus of claim 16 wherein said mounting arrangement further comprises an operating strand extending through said base and manipulable supports and a strand motive means capable of rotating said strand with respect to said manipulable support.

21. The apparatus of claim 16 wherein said mounting arrangement further comprises an operating strand extending through said base and manipulable supports and a strand motive means capable of translating said strand with respect to said manipulable support.

22. The apparatus of claim 18 wherein each of said base link axes extend tangentially along a circular circumference of a corresponding circle centered in said base support, and each said base link axis being tangent to that said circle at a point separated from another such point adjacent thereto by an angle substantially equal to 360° divided by that total number of said pivoting links in said first group of pivoting links.

23. The apparatus of claim 20 wherein said strand has a sleeve thereabout between said base and manipulable supports.

24. The apparatus of claim 21 wherein said strand has a sleeve thereabout between said base and manipulable supports.

25. A controlled relative motion system permitting a controlled motion member, joined to another base member, to selectively move with respect to that base member, said system comprising:

a base support;

a manipulable support;

a plurality of force imparting means coupled to said base support;

a group of at least four link end constrainers each having a first portion movably connected to a second portion thereof such that ends of said first and second portions can be selectively separated from one another along a selected direction so as to have a selected distance therebetween;

a first group of at least four pivoting links at least one of which is rotatably coupled to a corresponding said force imparting means that can impart force thereto so as to be rotatable about a corresponding base link axis and each coupled to a said first portion end of a corresponding one of said group of link end constrainers; and a second group of at least four pivoting links each rotatably coupled to said manipulable support so as to be rotatable about a corresponding support link axis and each coupled to a said second portion end of a corresponding one of said group of link end constrainers.

26. The apparatus of claim 25 wherein each of said first group of said pivoting links coupled to said base support is rotatably coupled to said base support through use of a pin extending in said base support and that said pivoting link and about which rotation can occur by at least one of said base support and that said pivoting link.

27. The apparatus of claim 25 wherein each of said first group of pivoting links is rotatably coupled to said first portion of a corresponding one of said group of link end constrainers so that said first portion is rotatable about a corresponding constrainer link axis, each of said pivoting links in said first group thereof is coupled to said base support so as to be rotatable about a corresponding base link axis, each of said first group of pivoting links having said corresponding base link axis thereof extending in a direction differing from that in which said corresponding constrainer link axis extends, each of said first group of pivoting links having said corresponding base link axis thereof and said corresponding constrainer link axis extending in different directions than do said corresponding base link axis and said corresponding constrainer link axis of another of said first group of pivoting links, each of said base link axes extending tangentially along a circular circumference of a corresponding circle centered in said base support, and each said base link axis being tangent to that said circle at a point separated from another such point adjacent thereto by an angle substantially equal to 360° divided by that total number of said pivoting links in said first group of pivoting links; and wherein each of said second group of pivoting links is rotatably coupled to said second portion of a corresponding one of said group of link end constrainers so that said second portion is rotatable about a corresponding constrainer link axis, each of said second group of pivoting links having said corresponding constrainer link axis extending in a direction differing from that in which said corresponding support link axis thereof extends, each of said second group of pivoting links having said corresponding constrainer link axis and said corresponding support link axis thereof extending in different directions than do said corresponding constrainer link axis and said corresponding support link axis of another of said second group of pivoting links.

28. The apparatus of claim 27 wherein each of said base link axes extend into regions between adjacent ones of said first group of pivoting links into which regions said base link axes of said adjacent ones also extend.

29. The apparatus of claim 28 where one of said first plurality of pivoting links has said base link axis thereof and said holding link axis thereof each oriented substantially perpendicular to planes which intersect one another at substantially right angles.

* * * * *